(12) United States Patent
Iida et al.

(10) Patent No.: US 6,180,347 B1
(45) Date of Patent: Jan. 30, 2001

(54) METHOD FOR MONITORING TRANSCRIPTIONAL SYNTHESIS OF RNA

(75) Inventors: Yukari Iida, Shizuoka; Hiroyuki Koshimoto, Kanagawa; Satoshi Kondo, Aichi; Akihiko Tsuji, Shizuoka, all of (JP)

(73) Assignee: Laboratory of Molecular Biophotonics, Hamakita (JP)

( * ) Notice: Under 35 U.S.C. 154(b), the term of this patent shall be extended for 0 days.

(21) Appl. No.: 09/269,519

(22) PCT Filed: Feb. 3, 1998

(86) PCT No.: PCT/JP98/00444

§ 371 Date: Apr. 2, 1999

§ 102(e) Date: Apr. 2, 1999

(87) PCT Pub. No.: WO98/33897

PCT Pub. Date: Aug. 6, 1998

(30) Foreign Application Priority Data

Feb. 3, 1997 (JP) .................................................. 9-020632

(51) Int. Cl.[7] .............................. C12Q 1/68; C12P 19/34
(52) U.S. Cl. ............................ 435/6; 435/91.1; 435/91.3; 435/91.5
(58) Field of Search .............................. 435/6, 91.1, 91.3, 435/91.5

(56) References Cited

U.S. PATENT DOCUMENTS

| | | |
|---|---|---|
| 4,996,143 | 2/1991 | Heller et al. ............................ 435/6 |
| 5,814,447 * | 9/1998 | Ishiguro et al. ........................ 435/6 |

FOREIGN PATENT DOCUMENTS

| | | |
|---|---|---|
| WO 95/03428 | 2/1995 | (WO) . |
| WO 98/13524 | 4/1998 | (WO) . |

OTHER PUBLICATIONS

Amersham Life Science catalog, "Multicolor Fluorescent Reagents and Directly Labeled Biologicals" (date unknown).

Brown et al., "Modern machine–aided methods of oligodeoxyribonucleotide synthesis," in *Practical Approach Series: Oligonucleotides and Analogues* (Eckstein F, ED.), pp. 1–24 (IRL Press at Oxford University Press, Oxford, England (ISBN 0–19–963279–0) 1991).

Cardullo et al., *Poc. Natl. Acad. Sci. USA*, 85, 8790–8794 (Dec. 1988).

Chiang et al., *The Journal of Biological Chemistry*, 266 (27), 18162–18171 (Sep. 25, 1991).

"DNA–Dependent RNA Polymerases," in *Current Protocols in Molecular Biology*, Unit 3.8, Chapter 3 (John Wiley & Sons, 1996).

Jolly et al., *Experimental Cell Research*, 238, 299–304 (1998).

Zuker et al., *Nucleic Acids Research*, 9 (1), 133–148 (1981).
Ishiguro et al., *Nucleic Acids Research*, 24 (24), 4992–4997 (1996).

* cited by examiner

Primary Examiner—Kenneth R. Horlick
(74) Attorney, Agent, or Firm—Leydig, Voit & Mayer, Ltd.

(57) ABSTRACT

This invention provides a method for monitoring the transcriptional synthesis of RNA, and to an apparatus therefor. Specifically, the invention resides in monitoring the initiation and termination of a transcription reaction for RNA synthesis, as well as the synthesis of full-length RNA by measuring the fluorescence of a pair of oligonucleotide probes of two types having a base sequence that continuously hybridizes to a part of a base sequence of the RNA synthesized by transcription, the pair of oligonucleotide probes comprising a donor probe labeled with an energy donor fluorescent molecule and an acceptor probe labeled with an energy acceptor fluorescent molecule.

4 Claims, 23 Drawing Sheets

THREE-WAVELENGTH MEASUREMENT

SIMPLIFIED DIAGRAM OF APPARATUS FOR MONITORING IN VITRO TRANSCRIPTION REACTION OF MICROPLATE READER TYPE

METHOD FOR MONITORING TRANSCRIPTIONAL SYNTHESIS OF RNA

TECHNICAL FIELD OF THE INVENTION

This invention relates to a method for monitoring the transcriptional synthesis of RNA and to a device therefor.

BACKGROUND OF THE INVENTION

Proteins are synthesized on ribosomes based on the base sequences of RNA that are transcribed from those of DNA. Transcription reaction is the first stage toward protein synthesis and refers to a process that transcribes base sequences of DNA present within cell nuclei and synthesizes RNA. Specifically, it is a reaction that synthesizes complementary RNA from DNA, which serves as a template (i.e., adenine to uracil, or guanine to cytosine), in the 5'- to 3'-direction.

After RNA polymerase that is responsible for RNA synthesis has bound to a specific base sequence on DNA which is referred to as "promoter," it incorporates nucleotide triphosphates (NTP), which are complementary to the DNA bases, from the site of transcription initiation on the template DNA and it synthesizes RNA. Polymerization proceeds a few nucleotides away from the site of transcription initiation; and then, stable polymerization continues and the RNA strand is further elongated, separating from its DNA pairing. This series of polymerization reactions continues until a specific terminator sequence on the DNA appears.

In vitro transcription reaction is a process that utilizes the transcription mechanism in the cells and synthesize RNA in vitro with simplicity, and it requires RNA polymerase, cofactors thereof, NTP substrates, and template DNA.

In recent years in vitro transcription reactions utilizing T7, T3 and SP6 polymerases, which do not require the transcription cofactors, have been in frequent use. The in vitro transcription reaction utilizing T7, T3, or SP6 polymerase is a method to synthesize the desired RNA strand: it introduces a DNA fragment, which will serve as the template, into the downstream of each promoter, and carries out a transcription reaction by utilizing an RNA polymerase that specifically recognizes the promoter.

The in vitro transcription reaction allows the synthesis of RNA into which a cap structure or an intron is introduced in addition to that of long-strand RNA, both of which are difficult to achieve through automated synthesizers. These RNAs are in wide use as template RNA for in vitro translation or as probes for hybridization. The RNA to which a cap structure has been appended or that into which an intron has been introduced is used to analyze the termini or intervening sequences of transcripts. (Current Protocols in Molecular Biology, Green Publishing Associates, Inc. and John Wiley & Sons, Inc. 1996.)

Thus, in vitro transcription reactions for RNA synthesis are utilized in many research fields. However, a variety of conditions generally need to be precisely satisfied in order to allow an in vitro transcription reaction to proceed normally: among others, a promoter is to be incorporated into a suitable site on the DNA that is used as a template and the combination of the promoter and RNA polymerase must be appropriate. Also, for the purpose of carrying out the transcription reaction efficiently in a prepared sample, there is a need for setting detailed conditions, such as the quantity ratio of the template DNA to the RNA polymerase, to optimum values. Whether the sample prepared to carry out the in vitro transcription reaction satisfy the conditions can not be known until the reaction is actually conducted and the result is analyzed to determine whether the desired product has been produced. In practice, after the reaction solution is sampled at predetermined intervals and RNA is extracted, the absorption value at 260 nm is measured: this confirms that the quantity of the synthesized RNA in the reaction solution has increased, which is routinely used to determine whether the reaction has proceeded. Further, to ascertain that the synthesized RNA is of full-length, the determination is routinely made by the electrophoresis method after the RNA is extracted. These methods require manipulations for extracting the synthesized RNA, and the procedure therefor is normally very complicated and also time-consuming. Thus, the procedure must be repeated to determine conditions that allow the in vitro transcription reaction to proceed efficiently without irregularities, which requires a great amount of time and labor.

Known as a method for the detection of a nucleic acid such as single-stranded DNA is that which utilizes two types of fluorescence-labeled probes that hybridize with said nucleic acid. This comprises adding to a solution containing the nucleic acid, two types of probes labeled with fluorescent dyes that differ from each other in their kinds; and it takes advantage of the fact that when the two types of probes hybridize to the same nucleic acid adjacently to each other, the distance between the fluorescent dyes becomes shorter and thus, resonance energy transfer occurs between the fluorescent dyes with the result of changes in fluorescence spectra. (Cardullo, R. A. et al. (1988) Proc. Natl. Acad. Sci. USA. 85, 8790–8794 and U.S. Pat. No. 4,996,143 (Heller et al.)). When this method is applied to the detection of single-strand RNA, it is necessary that any site (a base sequence) on the RNA to which the probe can hybridize be searched in advance through experiments. Generally, RNA having not less than tens of bases in length adopts a specific stereostructure (secondary structure) in aqueous solution, and as a result, most sites in the RNA do not undergo hybridization with other nucleic acids. (Chiang, M. -Y., Chan H. et al., J. Biol. Chem. 266, 18162–18172, (1991).) Techniques for determining the sites on RNA to which probes can hybridize with reliability have not been established. Generally, the secondary structure of the RNA is simulated by computer (Michael Zucker and Patrick Stiegler, Nucleic Acid Research, 9, 133–148, 1981); in the predicted structure, candidates for the site to which the probe can hybridize are picked up; probes having their base sequences are prepared; and the presence or absence of hybridization between the respective probes and the RNA is determined experimentally. These manipulations are very complicated and need a great amount of time as well. Also, even if these manipulations are repeated, it is not necessarily guaranteed that any site that will hybridize to said RNA can be located. For these reasons, there has been no report of the case where RNA having not less than 100 bases in length was detected according to said method.

BRIEF SUMMARY OF THE INVENTION

This invention has remedied the above-mentioned drawbacks and provides a method for monitoring a transcription reaction for RNA synthesis on time without requiring either manipulations for RNA extraction or operations in electrophoresis. Specifically, it provides a method for monitoring the initiation, the progression, and the termination of the transcription reaction for RNA synthesis, as well as the quantitation of the total RNA to be synthesized by the method described above and the synthesis of full-length RNA. Further, it provides a method capable of measuring reaction rates with regard to the transcription reaction (the speed of rotation of the transcription) and of optimizing conditions for the reactions described above.

Furthermore, this invention provides a monitoring apparatus relying on the methods.

DESCRIPTION OF THE PREFERRED EMBODIMENTS

Figure 1A:
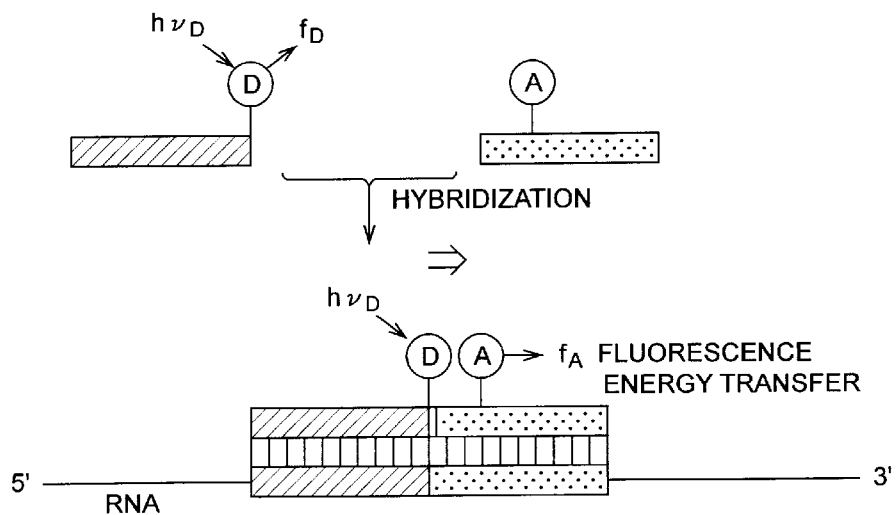
FIG. 1A shows probes for use in the monitoring methods according to this invention.

Specifically, this invention provides a method for monitoring the initiation and termination of a transcription reaction for RNA synthesis, as well as the synthesis of full-length RNA, the method comprising:

measuring the fluorescence of a pair of oligonucleotide probes of two types having a base sequence that consecutively hybridizes to a part of a base sequence of the RNA synthesized by transcription in a system of transcription reaction for RNA synthesis, wherein the pair of oligonucleotide probes comprises a donor probe labeled with an energy donor fluorescent molecule and an acceptor probe labeled with an energy acceptor fluorescent molecule.

Also, the invention provides a method for quantitation RNA transcription through a transcription reaction for RNA synthesis, the method comprising:

measuring the fluorescence of a pair of oligonucleotide probes of two types having a base sequence that consecutively hybridizes to a part of a base sequence of the RNA synthesized by transcription in a system of the transcription reaction for RNA synthesis, wherein the pair of oligonucleotide probes comprises a donor probe labeled with an energy donor fluorescent molecule and an acceptor probe labeled with an energy acceptor fluorescent molecule.

Also, the invention provides a method for simultaneously monitoring the initiation of transcription and full-length RNA in a transcription reaction for RNA synthesis, the method comprising:

measuring the fluorescence of at least two pairs of oligonucleotide probes of two types having a base sequence that consecutively hybridizes to a part of a base sequence of the RNA synthesized by transcription in a system of the transcription reaction for RNA synthesis, wherein the pair of oligonucleotide probes comprises a donor probe labeled with an energy donor fluorescent molecule and an acceptor probe labeled with an energy acceptor fluorescent molecule.

Further, the invention provides an apparatus for monitoring an in vitro transcription reaction for RNA synthesis, the apparatus comprising:

a device for synthetic reaction, said device carrying out the RNA transcription reaction;

a means for introducing a sample, said means introducing a sample solution from the device for synthetic reaction;

a device for mixing solvent (a device for preparing a sample to be measured), said device adjusting a concentration of the sample solution; and a device for measuring fluorescence. More specifically, this invention relates to the following: a method for monitoring the initiation and progression of an RNA transcription reaction, as well as the synthesis of full-length RNA; a method for quantitating the total quantity of RNA to be synthesized by the foregoing methods, as well as for monitoring the synthesis of the full-length RNA; a method for measuring the rate of the transcription reaction (the speed of rotation of the transcription); a method capable of optimizing the reaction conditions described above; and an apparatus for monitoring the RNA to be synthesized by the transcription reaction and, at the same time, quickly determining optimum conditions for the reaction, said apparatus utilizing the monitoring methods.

Figure 1B:
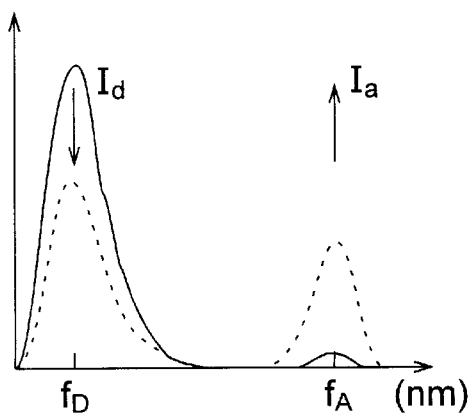
FIG. 1B is a graph schematically showing the change in the fluorescence spectrum observed in a monitoring method according to the invention.
Figure 2:
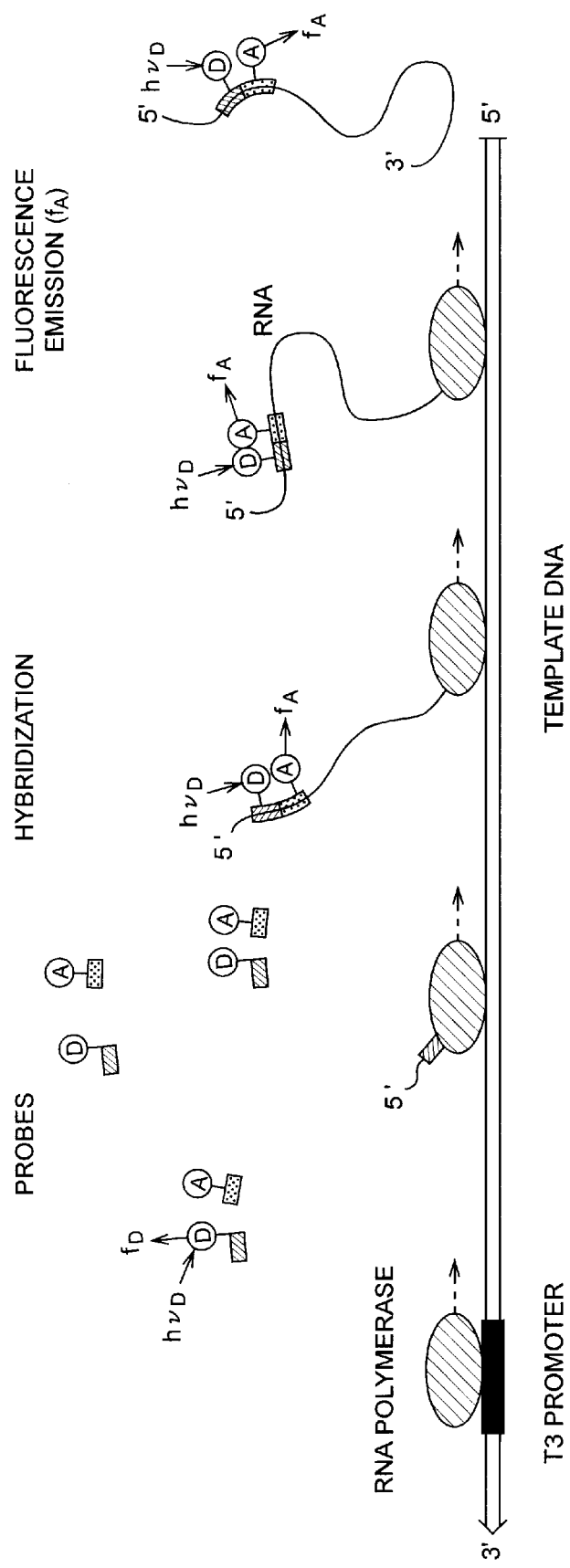
FIG. 2 shows the outline of the methods for monitoring a transcription reaction for RNA synthesis according to the invention.

The outline of the methods according to this invention is illustrated in FIGS. 1A, 1B, and 2. Specifically, they are enabled by the following: probes having a base sequence complementary to at least a part within the base sequence of RNA to be synthesized by transcription reaction are added to a reaction solution and are hybridized to the RNA being synthesized; and the fluorescence spectrum of the hybrid is to be measured. Here, for the probes to be used in the methods according to the invention, two types of fluorescence-labeled probes are employed as a pair. One of the probes is labeled with an energy transfer donor fluorescent dye and the other labeled with an energy transfer acceptor fluorescent dye; and each of them has a base sequence capable of continuously hybridizing to a specific part of the above-mentioned RNA (FIG. 1A). When the probes (the pair of probes of two types) adopt a specific spatial configuration by being hybridized to the RNA, the spatial distance between the donor and acceptor dyes is within about 80 Å; under these conditions, energy transfer to the acceptor dye will occur with certain probability if the donor dye is excited by light, and as a result, the fluorescence from the acceptor dye will be observed (FIG. 1B). (Cardullo, R. A. et al. (1988) Proc. Natl. Acad. Sci. USA. 85, 8790–8794.) It is known that the energy transfer is an interaction that occurs in the manner depending on the distance between donor and acceptor and that it does not occur substantially if the distance is not less than 80 Å apart. Therefore, fluorescence from the acceptor dye is not observed in a state where there is no hybridization to the RNA.

In other words, the donor fluorescence (expressed as fluorescence intensity Id) is strong and the acceptor fluorescence (expressed as fluorescence intensity Ia) is weak when the probes do not undergo hybridization. When the probes do undergo hybridization, the donor fluorescence grows weak and the acceptor fluorescence strong. Accordingly, by taking the ratio of the fluorescence intensity of donor (Id) to that of acceptor (Ia), it is possible to determine the presence of the partial sequence of the RNA to which the probes hybridize, as well as to quantitate the existing quantity of the RNA.

As FIG. 2 schematically illustrates, the probes are added to a reaction system that synthesizes RNA through transcription reaction: under the conditions, once the RNA synthesis is initiated by RNA polymerase and the partial sequence capable of hybridizing to the probes is produced, hybridization of the probes results. As explained above, this result is that the fluorescence intensity of donor decreases and the fluorescence intensity of acceptor increases.

With respect to the probes to be used here, any part of RNA to be synthesized can be selected as the site at which they are allowed to hybridize to the RNA. Namely, in FIG. 2 a large quantity of probes is contained in the reaction solution for the synthesis; therefore, once the site having a base sequence complementary to the probes is synthesized as individual RNA molecules are being synthesized, the probes immediately hybridize to it. Consequently, in the practice of the method shown schematically in FIG. 2 even if probes are employed which correspond to the site that causes no hybridization when they are added after the RNA has formed a specific stereostructure, they can be hybridized to the RNA.

Also, it is possible to select such combination of a donor dye and an acceptor dye that will satisfy the condition where the donor fluorescence is hardly observable at the wavelength of the acceptor fluorescence. Under this condition, it becomes possible to determine the presence of the synthesized partial sequence of RNA and to quantitate it by observing the fluorescence intensity of the acceptor dye.

Further, although the probes according to this invention are explained as those having a base sequence capable of continuous hybridization, they are not limited thereto. Where two types of probes according to the invention have such base sequence that hybridizes to part of RNA adjacently to each other, they can be effectively used if a significant change is caused in the fluorescence spectrum at the time of hybridization. Where the two types of probes for use in the invention are hybridized too far apart, there will be less probability that the fluorescence energy transfer as described previously occurs; and substantially, the change in the fluorescence spectrum will no longer be observed.

Explanation will be made in more detail. The two types of probes described previously are added to a transcription reaction solution for in vitro RNA synthesis. The transcription reaction takes place and the synthesis of RNA is initiated to produce its part capable of hybridizing to the probes; and then, the pair of probes continuously hybridizes to the adjacent sites. Upon hybridization energy transfer occurs between the aforementioned dyes and the fluorescence spectrum changes. The fluorescence observed from a sample is a mixture of fluorescence from the probes hybridized to the RNA and fluorescence from the probes existing in the reaction solution in their free state. As the proportion of the probes, which have hybridized to the RNA, to the total probes becomes greater, so does the degree of change in the fluorescence spectrum. Namely, the spectral change grows larger as the quantity of the RNA being synthesized increases. Here, assuming that the ratio of the fluorescence intensity of donor at its fluorescence wavelength (Id) to that of acceptor at its fluorescence wavelength (Ia) is, for example, taken in a fluorescence spectrum, the Ia/Id value will increase with increasing quantities of the RNA being synthesized.

Figure 3A:
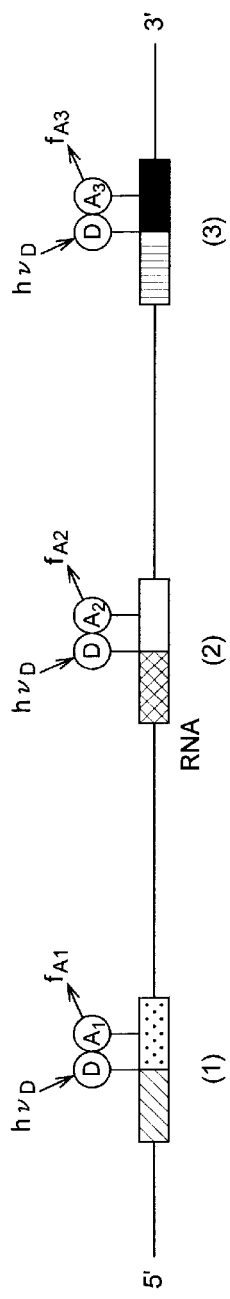
FIG. 3A represents the embodiment where plural pairs of probes are employed in the monitoring methods according to the invention, the representation schematically showing the manner in which probes having a base sequence complementary to the vicinity of the 3'-terminus of RNA to be synthesized, those having a base sequence complementary to the intermediate part of the RNA to be synthesized, and those having a base sequence complementary to the vicinity of the 5'-terminus of the RNA to be synthesized are respectively hybridized onto the RNA.

Now, probes having a base sequence that hybridizes to a base sequence in the vicinity of the 5'-terminus of RNA to be synthesized are supposed to be used (the section as indicated by (1) in FIG. 3A). In this case, it becomes possible to monitor the initiation of a transcription reaction by measuring a change in the fluorescence spectrum. When the ratios (Ia/Id) are plotted against time, the rate of increase of the Ia/Id value represents the speed of rotation of the transcription reaction. Namely, with regard to a prepared sample and its use conditions the following can be found out: (1) whether a transcription reaction takes place; and (2) the speed of rotation of the reaction (the degree of suitability of the reaction conditions).

Also, if probes that hybridize to a base sequence of the intermediate part of the RNA to be synthesized are used (the section as indicated by (2) in FIG. 3A), it becomes possible to monitor elongation of the RNA synthetic reaction. Further, if probes that hybridize to a base sequence in the vicinity of the 3'-terminus of the RNA to be synthesized are used (the section as indicated by (3) in FIG. 3A); it is possible to monitor the synthesis of full-length RNA. It often happens that even if the transcription reaction is initiated, RNA of incomplete length is synthesized for various reasons such as contamination by incomplete template DNA. To determine whether the full-length RNA is synthesized, the prior art methods require that products are separated by electrophoresis and their lengths are ascertained. If the probes that hybridize to the vicinity of the 3'-terminus are used to practice this invention, it is possible to determine on the full-length RNA on time.

In order to obtain optimum reaction conditions for a sample prepared for the purpose of carrying out RNA synthesis through transcription reaction; the following method for use is feasible, for example. First, probes that hybridize to the vicinity of the 5'-terminus are used to determine whether the transcription reaction takes place. Further, the rate of the transcription reaction is monitored, and conditions are set so as to produce the highest reaction rate. Next, probes that hybridize to the vicinity of the 3'-terminus are used to confirm that full-length RNA has been synthesized under the conditions thus set.

Figure 3B:
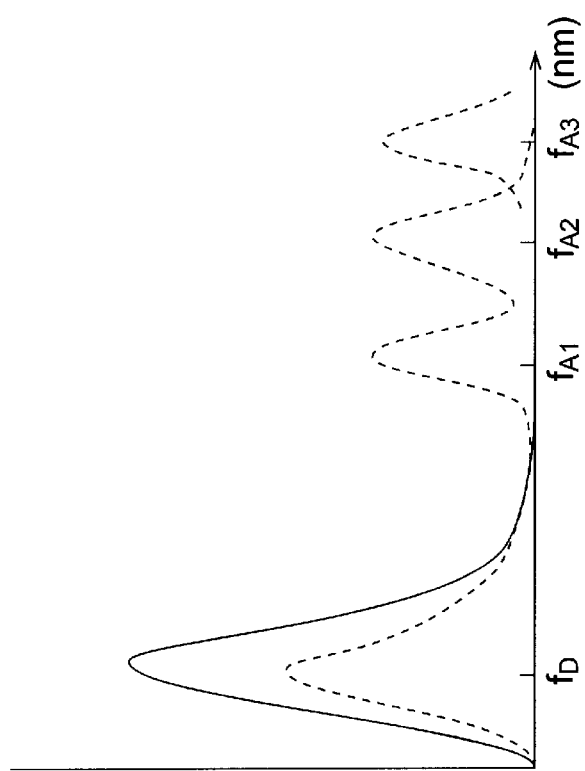
FIG. 3B is a graph schematically showing the fluorescence spectra resulting from hybridization of the respective probes.

A variety of combinations of donor/acceptor fluorescent dyes that causes energy transfer exists, and the use of any combination of dyes is possible because the methods according to this invention do not rely on the combination of dyes. Therefore, combinations of two or more pairs of dyes can be used at the same time (FIG. 3B). For example, probes that hybridize to the vicinity of 5'-terminus are labeled with a specific kind of donor/acceptor fluorescent dyes and probes that hybridize to the vicinity of 3'-terminus are labeled with another kind of donor/acceptor fluorescent dyes. By adding these to a reaction solution at the same time, it is possible to simultaneously confirm the occurrence or nonoccurrence of the initiation of a transcription reaction, as well as the synthesis of fill-length RNA.

The quantities of probes to be added to the reaction solution can be set arbitrarily in the present methods. Specifically, it is possible to add a 10-fold (molar ratio) or 1000-fold quantity that of template DNA. When a 10-fold quantity is added, the fluorescence spectrum changes within the range where the quantity of the synthesized RNA is up to tenfold that of the template DNA. Even if RNA is synthesized above that, the fluorescence spectrum will not change more: Since the probes have all hybridized to the synthesized RNA and no free probes are present in the reaction solution, there are no probes that can hybridize to the newly synthesized RNA. Thus, when the probes are added in a small excess to the template DNA and the reaction is initiated, the initial stage of the transcription reaction can be monitored with great accuracy. This is suitable when probes that hybridize to the vicinity of 5'-terminus are used to find out the presence or absence of the transcription reaction, as well as to determine its rate. On the other hand, when a 1000-fold quantity is added, the fluorescence spectrum changes within the range where the quantity of the synthesized RNA is up to 1 000-fold that of the template DNA. For example, if the synthetic reaction practically ends at the point where it has produced less than a 1000-fold quantity of RNA based on the template DNA, the time-dependent change in the fluorescence spectrum stops at that point. Therefore, it is suitable for the monitoring of termination of the synthetic reaction. Thus, conversely, when the probes are added in a large excess to the template DNA and the reaction is initiated, the change in the fluorescence spectrum at the initial stage of the reaction (when the quantity of the synthesized RNA is small) is so little that its measurement with great accuracy may be difficult. In other words, when the initial stage of the reaction, e.g., the occurrence or nonoccurrence of the transcription reaction, is monitored, a small excess of probes may be added to the template DNA; whereas, when the later stage, e.g., the occurrence or nonoccurrence of the termination of reaction, is intended to be monitored, the probes are added in a large excess to the template DNA.

Structure of Probes

Insofar as the base sequence of a probe according to this invention is that which is provided with a base sequence substantially complementary to the site that is any part of RNA to be synthesized, it is not particularly limited. Namely, it is unnecessary to previously determine through experiments as to whether said probe hybridizes with said RNA synthesized. Needless to mention, any base sequence that hybridizes to the synthesized RNA may be experimentally searched for, and probes having that base sequence may be used. Also, as for the length of base, it is not particularly limited insofar as said probe satisfies the requirement of specifically hybridizing to said RNA in a substantial manner. This length is normally 15 bases or more.

There are no particular limitations to the type of fluorescence dye for the probes according to the invention, namely the kind of a combination of donor and acceptor fluorescence dyes; but the combinations in which the critical transfer distance in energy transfer (the distance at which the energy transfer efficiency reaches 50%) is long are preferable, since the changes in fluorescence spectra resulting from the energy transfer are large. For example, the combination in which a fluorescein type dye is the donor and a Rhodamin type dye is the acceptor can preferably be used. Preferably, usable as an energy donor fluorescent molecule are fluorescent dyes of the BODIPY type (4,4-difluoro-4-bora-3a,4a-diaza-s-indacene, Molecular Probes Inc.), the fluorescein type, and the Rhodamin type, for example; and particularly, fluorescent dyes of the fluorescein and Rhodamin types are preferable in this invention. Dyes of the Indocyanin and Rhodamin types can preferably be used as an energy acceptor fluorescent molecule; and particularly Cy5, Cy3, and Cy3.5 (Amersham Life Science, FluoroLink, Cat. No. PA25001, PA23001, and PA23501) in addition to Rhodamin are preferable in the invention.

Further, groups binding the fluorescent dyes to probes are not particularly limited in the invention; and the binding can be done through suitable linkers, which are of such type that the probes maintain sufficient water-solubility, so that the two types of fluorescent dyes may cause the desirable fluorescence energy transfer. For example, tetramethylene to decamethylene chains are usable.

Furthermore, although the probes are explained by way of DNA (as oligonucleotides), they are not particularly limited to DNA. Various nucleotide derivatives are also usable and they only have to be able to specifically hybridize to a specific part of the base sequence on RNA in a substantial manner. Concretely, mentioned are RNA, oligonucleotides of the phosphorothioate type (S-oligo), oligonucleotides of the methylphosphonate (M-oligo), oligonucleotides of the phosphoroamidate type (A-oligo), peptides, and nucleic acids.

Methods of Probe Synthesis

There are no particular limitations to methods for preparing oligonucleotide sequence portions of the detection probes according to this invention, which have been explained above. Methods of nucleic acid synthesis known in the art can preferably be used. Particularly, a variety of automated synthetic methods based on the solid phase synthetic techniques are preferable, and for example, synthetic methods such as the amidite or triester methods are preferably used. (Edited by F. Eckstein, Modem machine-aided methods of oligodeoxyribonucleotides synthesis, Oligonucleotide and Analogues, IPL Press, 1991.)

Further, methods of introducing to a probe, a preferable linker portion for the binding of a fluorescent dye are feasible by the use of various reagents for the modification of peptides. Particularly in this invention, 6-(trifluoroacetylamino)-hexyl-(2-cyanoethyl)-(N,N-diisopropyl)-phosphoroamidite, which is a reagent for the amination of 5'-termini, can be used simultaneously with the chemical syntheses as described above. This enables the introduction of a hexylamino group (after removal of a trifluoroacetyl group) to an arbitrary position of the oligonucleotide chain. Also, the probes, which allow the two types of fluorescent dyes to adopt the desired relative spatial configuration, are to be prepared by selecting the positions and the lengths of linker portions: for this purpose a variety of molecular models and computer programs for molecular modeling can be used to predict the spatial configuration. There are no particular limitations to the methods for binding a linker portion and a necessary probe or to the methods for binding said linker portion to the base at an appropriate position of an oligonucleotide probe; and those such as methods of chemical synthesis or enzymatic methods can be used.

Fluorescence-Measuring Device

There are no particular limitations to means for fluorescence measurements that can be used in this invention. Conventional fluorescence-measuring devices may preferably be used insofar as they generate excitation light that excites energy donor fluorescent dyes and can measure the fluorescence from energy donor fluorescent dyes and from energy donor fluorescent dyes.

Data Processing

As for processing of the data obtained by the fluorescence-measuring means, optimum processing methods, which depend on the kinds of dyes to be used, are applicable, and it is thus not particularly limited.

Where the fluorescence spectrum of an energy donor dye is chosen so that it may not hardly overlap the wavelength of the fluorescence of an energy acceptor dye to be observed, it becomes possible to use the time-dependent change in fluorescence intensity at the wavelength of fluorescence of the energy acceptor dye to be observed, as such. Namely, an effect due to the time-dependent change in the fluorescence from the energy donor dye at the wavelength of fluorescence of the energy acceptor dye to be observed proves to be a negligible level.

Apparatus for Monitoring In vitro Transcription for RNA Synthesis

Figure 4:
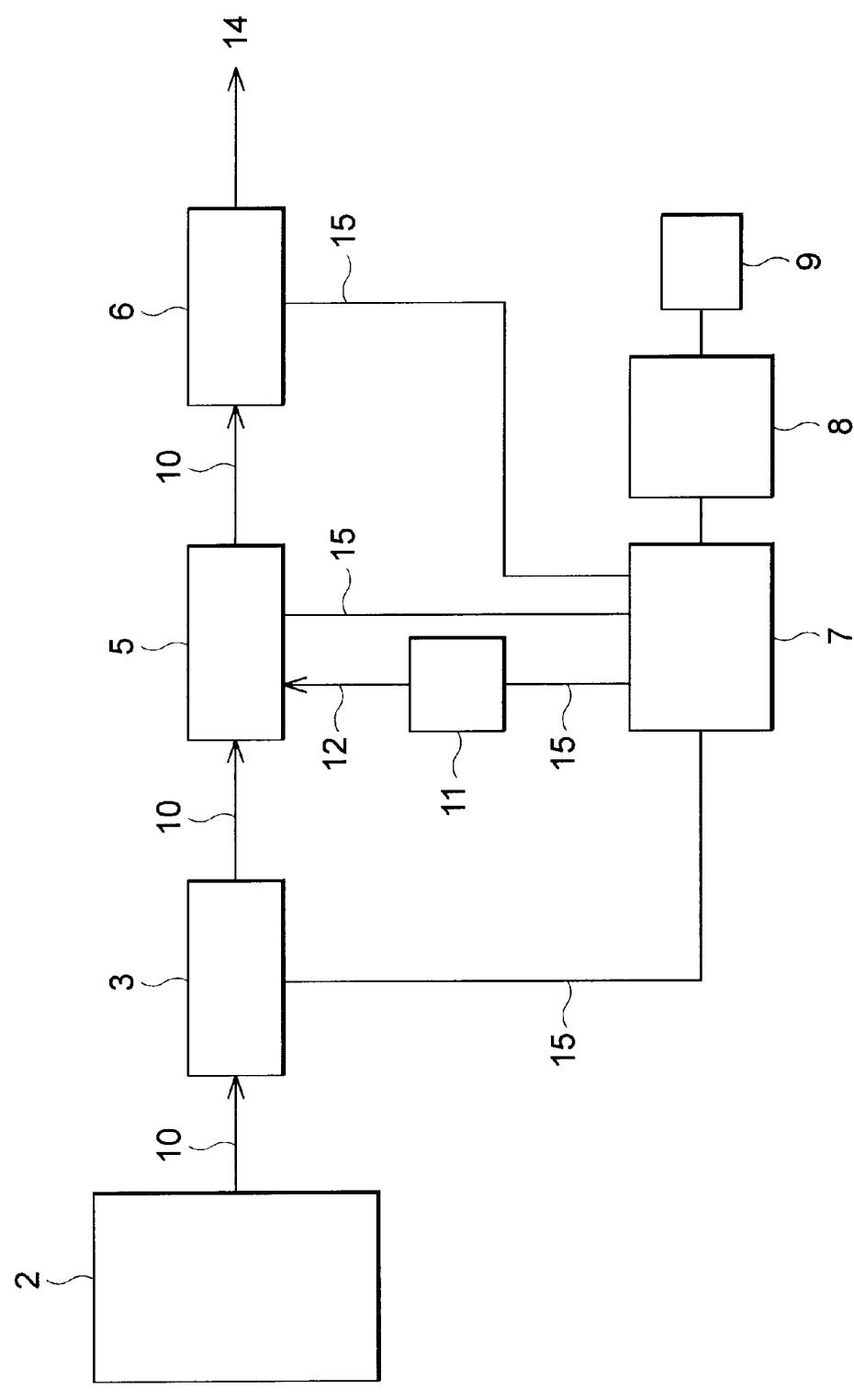
FIG. 4 is a diagram showing the outline of a monitoring apparatus according to the invention.

FIG. 4 illustrates an embodiment of the apparatus for monitoring the in vitro transcriptional synthesis of RNA, which utilizes the methods according to this invention. A sample introduction means 3 is a means for introducing part of the aforementioned reaction solution into a preparation device for a solution to be measured 5 through a suitable sampling line 10 from a reaction device of various types and sizes for the in vitro transcription for RNA synthesis 2. Here, the sample introduction means 3 can be controlled by a controller 7 with respect to the timing of sampling and the amounts of solution. The controller 7 also adds appropriate amounts of solvent from a solvent device 11 to the preparation device for a solution to be measured 5 through a solvent mixing line 12. Diluted samples in the preparation device for a solution to be measured 5 are introduced into a fluorescence-measuring device 6.

Where probes that have been confirmed by previous experiments to hybridize to synthesized RNA are used, an apparatus for monitoring synthesis in the following configuration is also usable. A probe preparation device, which introduces a probe kit, may be appended to the preparation device for a solution to be measured 5. Specifically, requisite types and concentrations of probe kits set by the controller 7 may be mixed and introduced from the probe preparation device into the preparation device for a solution to be measured 5 through a probe mixing line. The preparation device for a solution to be measured 5 may set the conditions of hybridization between the synthesized RNA and the probes in the sample solution, with the aid of the controller 7. Concretely they are a mixing cell of required volume, concentrations, and time. Further, if necessary there may be a device for stirring a mixed solution of sample and probes the stirring time and speed of which has been set by the controller 7. The probe preparation device selects the kinds of probes suitable for monitoring purposes and prepares a probe solution by diluting them to appropriate concentrations, and introduces it into the preparation device for a solution to be measured 5. At this juncture, the introduction is possible through a pressure or peristaltic pump or the like. After hybridization is effected in the preparation device for a solution to be measured 5, the fluorescence-measuring device 6 receives the introduction. Here, the fluorescence-measuring device 6 records fluorescence spectra according to the conditions of fluorescence measurements such as an excitation light condition, which have been set by the controller 7, and send the data obtained to a data processing device 8. The measured data consist of those of fluorescence spectra and their time-dependent changes in the case of excitation by predetermined excitation wavelengths. Means for incorporating data to the data processing device 8 can also store the data in a memory device inside the data processing device 8. On the basis of the data incorporated into the data processing device 8, confirmation of the initiation of transcription and the synthesis of full-length RNA in an in vitro transcription reaction for RNA synthesis is made by a program computing changes in the concentration of the transcribed RNA. Means for computing changes in the concentration of the transcribed RNA can also perform calculation based on calibration curves of the fluorescence intensities at predetermined wavelengths of respective energy acceptor probes and the concentrations of hybridized RNA (or the numbers of molecules), which have been previously stored in the memory device. In addition, the means described above can also be run automatically, according to a program that has been previously stored in the memory device (not shown in the figure), which is provided by the data processing device 8. Such program can be inputted to the memory device by an input/output device 9, but a program previously stored can also be read into it after having been selected from the input/output device 9. More specifically, the sampling line is opened at the time previously programmed, or by input from the input device, and part of a solution during the reaction is introduced into the monitor system. Then, a probe solution that has been previously provided by the controller is selected and introduced into the probe mixing device, and the sample solution and the probes, which are mixed, are maintained under hybridization conditions: the controller reads the parameters, previously stored, from the memory device within and sets the hybridization conditions. Subsequently, after hybridization is complete, the mixed solution is sent to the fluorescence spectrum measuring device for the measurement of fluorescence spectra at a prescribed time, and is irradiated with the excitation wavelength of an energy donor fluorescent dye, which has been set depending on the probes. At the same time fluorescence intensity at the fluorescence wavelength of each energy acceptor fluorescent dye, which has been set depending on the probes, is measured; and the measured data is stored in the memory device inside the controller. The stored, measured data is read out by the data processing device to determine the presence or absence of hybridization with respect to each probe, and the results are outputted. After measurement, the sample solution is discharged into a drain 14.

Figure 5:
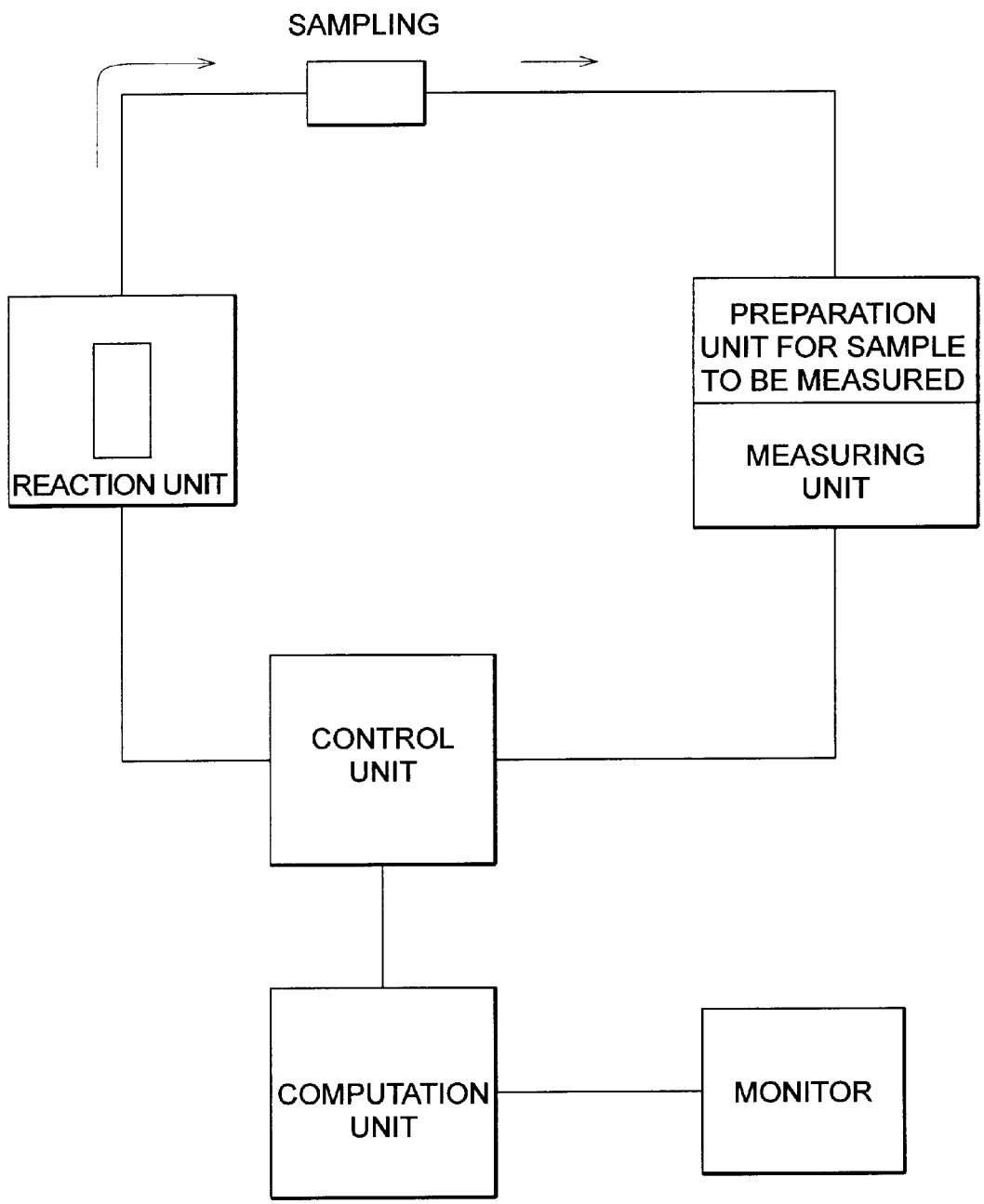
FIG. 5 is a diagram showing the construction of an apparatus for monitoring an in vitro transcription reaction for RNA synthesis according to the invention.
Figure 6:
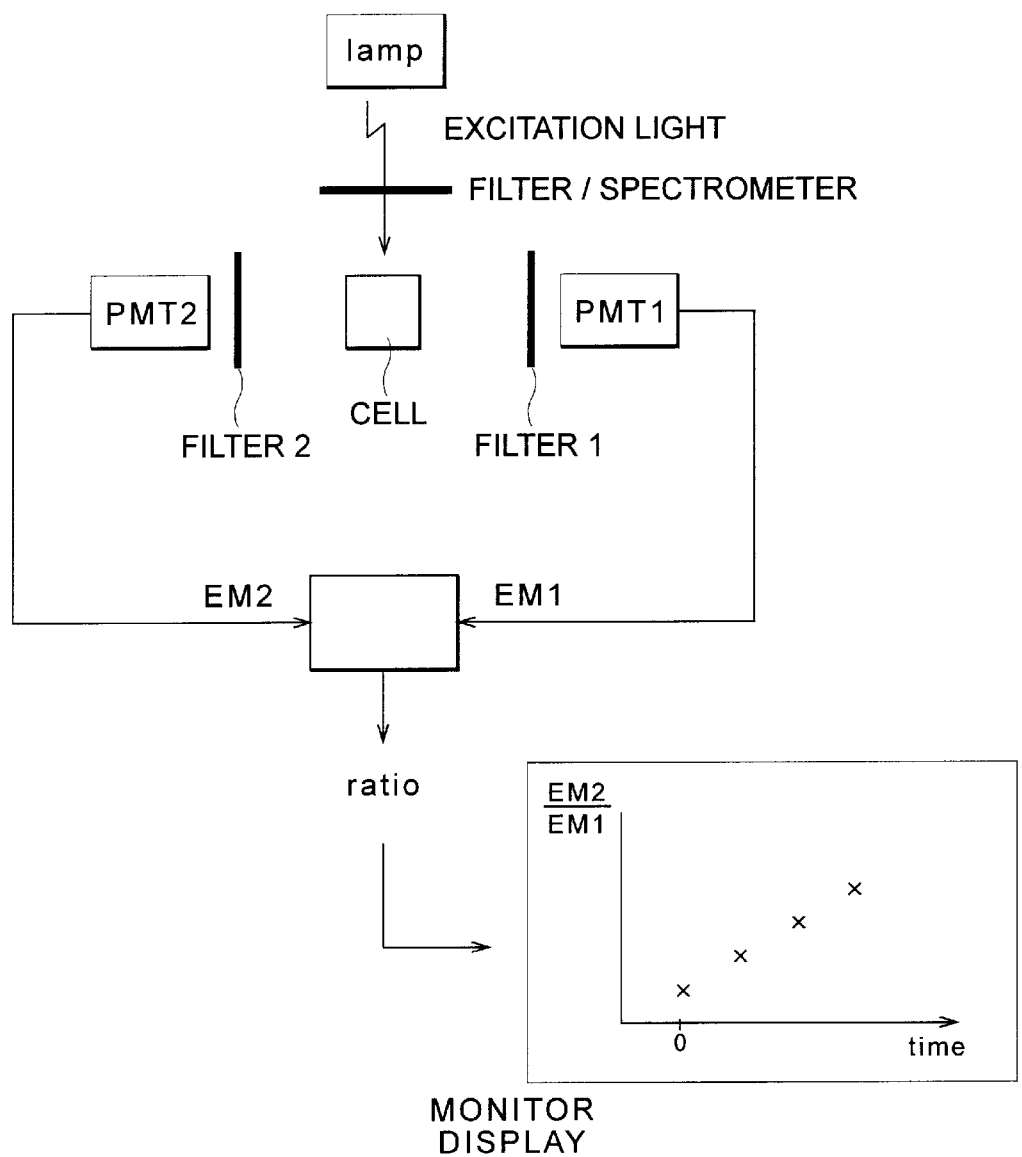
FIG. 6 is a diagram showing the construction of a measuring unit in the case where two-wavelength monitoring is performed with a pair of fluorescence-labeled probes.
Figure 7:
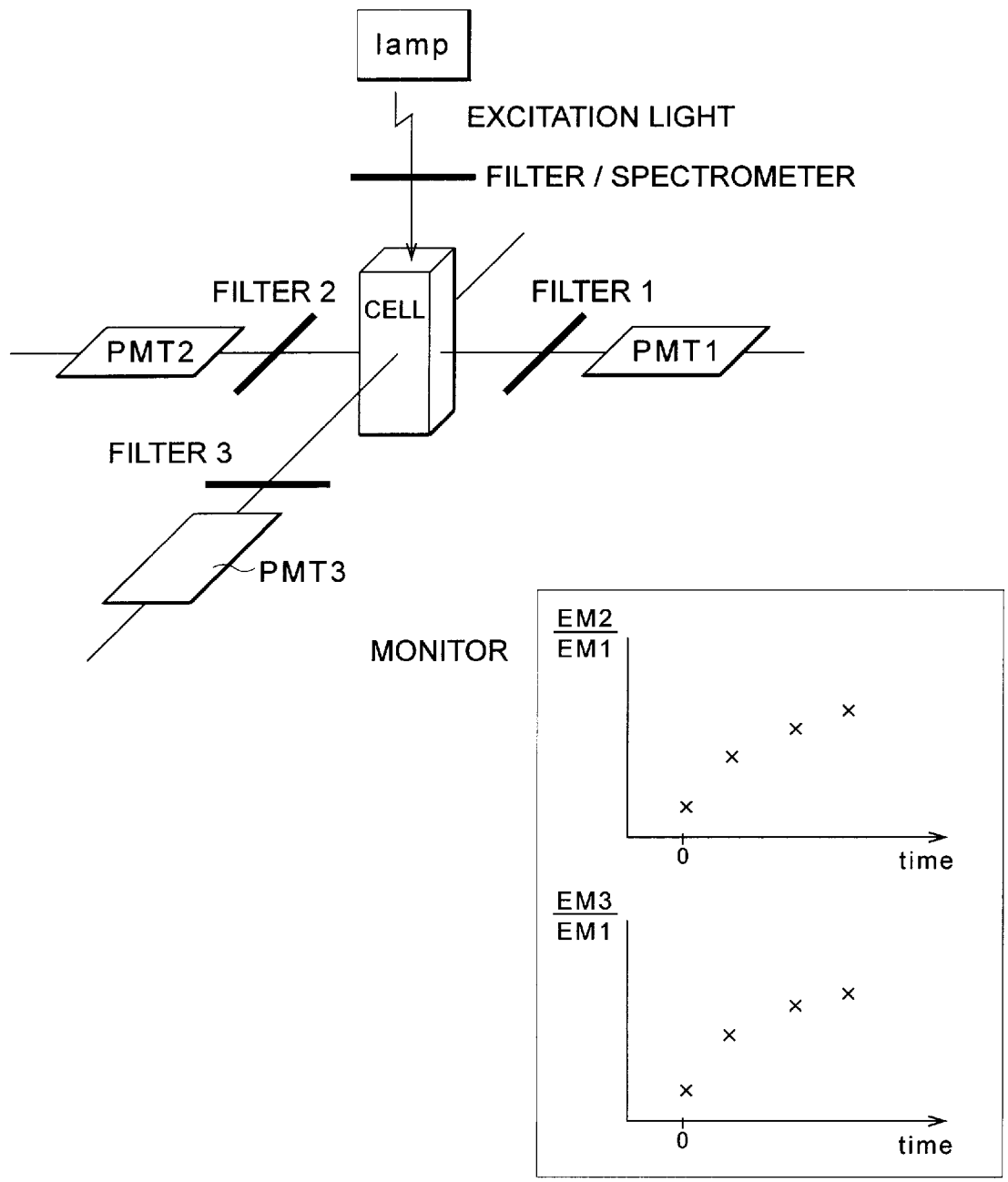
FIG. 7 is a diagram showing the construction of a measuring unit in the case where three-wavelength monitoring is performed with two pairs of fluorescence-labeled probes.

FIG. 5 illustrates a configuration of a more detailed apparatus for monitoring an in vitro transcription reaction for RNA synthesis. As shown in FIG. 5, the apparatus comprises a reaction unit, a sample preparation unit for measurement, a measuring unit, a control unit, a computing unit, and a monitor. The reaction unit is a unit that conducts the transcription reaction for RNA synthesis and consists of a reaction cuvette and a temperature control element for maintaining the reaction solution in the reaction cuvette at a constant temperature. To the reaction cuvette are added template DNA, probes, RNA polymerase, nucleotide triphosphates (ATP, GTP, CTP and UTP), and reaction buffer. Reaction is started (taken as t=0) by addition of RNA polymerase or the template DNA to that reaction solution. The reaction solution in the reaction cuvette is maintained at a constant temperature (e.g., 37° C.) by means of the temperature control element. A water bath, a hot plate or the like can be used as the temperature control element. After the reaction has started, aliquots of the reaction solution are collected at prescribed intervals and transferred to a measuring cuvette within the sample preparation unit for measurement. A predetermined amount of buffer is pipetted into the measuring cuvette in advance. Alternatively, a sample that has been sampled is transferred to a dilution cuvette and diluted by addition of a predetermined amount of diluting solution from a reservoir thereof; and thereafter, it may be transferred to the measuring cuvette. Sampling can be done manually, or may be automated. The sample preparation unit for measurement consists of a plurality of measuring cells that are circularly arranged. Individual measuring cells are located at any of one "sample input position," one "measuring position," and plural "stand-by positions." The sample that has been sampled is poured into a measuring cuvette located at the "sample input position." Thereafter the cuvette moves to the "measuring position." The cuvette, which has moved to the "measuring position," then moves to the measuring unit located at the lower part of the sample preparation unit for measurement. Fluorescence measurements are performed in the measuring unit. After the measurements, the cuvette returns to its original position in the sample preparation unit for measurement. This completes one cycle. Subsequently, once a sample that has been sampled from the reaction solution is again poured into a measuring cuvette located at the "sample input position," the next cycle begins. The arrangement of measuring cells in the sample preparation unit for measurement is not limited to be circular. The fluorescence measurement of a sample in the cuvette is performed in the measuring unit. As FIGS. 6 and 7 illustrate, the measuring unit consists of a light source for excitation light (a lamp or the like), a filter or spectroscope for fractionating by wavelength, the light from the light source, a measuring cell, a filter or photodetector (photomultiplier) for fractionating by wavelength, the fluorescence emitted by a sample in the measuring cell. The measuring cell moves from the sample preparation unit for measurement to its position in the measuring unit. The fluorescence emitted by the sample is detected in two- or three-directions simultaneously. Fluorescence intensities are measured in the respective directions through filters differing in their wavelength characteristics from each other. Where measurement is to be performed in the two-direction (FIG. 6), a filter 1 corresponds to the wavelength region allowing the donor fluorescence to transmit selectively and a filter 2, the acceptor fluorescence, respectively. Where two or more pairs of fluorescence-labeled probes is used to simultaneously monitor the initiation of a transcription reaction and the synthesis of full-length RNA, the fluorescence from the sample is detected in the three directions at the same time. In this case (FIG. 7), a filter 1 corresponds to the wavelength region allowing the donor fluorescence to transmit selectively; a filter 2, the fluorescence of one of two kinds of acceptors; and a filter 3, the fluorescence of the other kind of acceptors, respectively.

The fluorescence intensities (EM1, EM2, and EM3) measured by the photodetector are respectively sent to the computing unit and the fluorescence intensity ratios (EM2/EM1 and EM3/EMI) are calculated. These results are sent to the monitor to be displayed thereon. All the processes as described above are controlled by the control unit.

Figure 8:
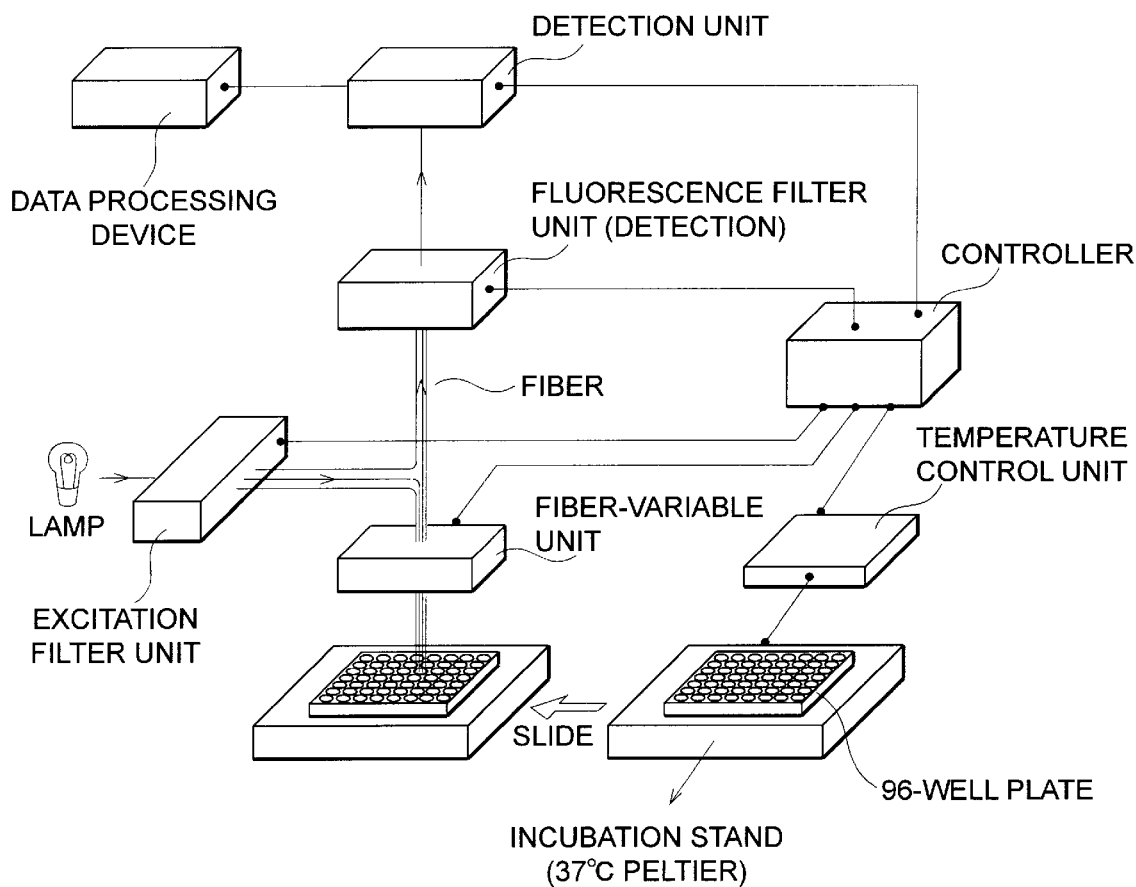
FIG. 8 is a diagram showing the construction of an apparatus for monitoring an in vitro transcription reaction for RNA synthesis according to the invention, which employs a 96-well plate.

Further, as another embodiment FIG. 8 illustrates a configuration of the apparatus for monitoring an in vitro transcription reaction for RNA synthesis, which is of a microplate reader type and utilizes the methods according to this invention.

An incubation stand fixes a 96-well plate and has an incubation function; and a controller may control its temperature adjustment. The plate and the incubation stand, after fixation of the plate, slide automatically through the control of the controller and are moved to a measuring position.

Both excitation filter and fluorescence filter units can have several kinds of excitation and fluorescence (detection) filters built-in, and devices for automatically setting filters on optical axes can also be built-in. When the excitation and fluorescence filters are selected through the controller, they are automatically set in holders on their optical axes. Then the filter holders can employ those of a multi-range type so that they may deal with a plurality of excitation or detection wavelengths. These holders can slide variably on the optical axes under control of the controller.

A fiber-variable unit moves the excitation light and fluorescence (detection light) fibers to the designated positions within the 96 wells when it receives from the controller, a signal indicating the start of measurement. At this juncture, the controller controls the positions to which the fibers move. Normally, when the start and end positions are inputted by the controller, the fibers move on the 96 wells, which makes it possible to analyze samples sequentially.

Through the process described above, when the excitation light irradiates one sample (i.e., one well) on the plate, the fluorescence passes within the fibers again to enter into the fluorescence filter unit, and only the fluorescence having a predetermined wavelength (the wavelength set by the filter) is picked.

Subsequently, the selected light enters into a detection unit, where the fluorescence intensities of donor and acceptor are measured. The series of processes thus far is performed at the intervals inputted by the controller. The resulting fluorescence intensities are converted into the ratios of fluorescence intensities by a data processing device; and if they are plotted against time, it is possible to monitor a transcription reaction automatically.

The examples of this invention will be explained below.

EXAMPLES

In the present examples XELF1-αDNA was all used as template DNA in transcription reactions to monitor the reaction for the synthesis of XELF1-αRNA. A MEGAscript T3 kit (available from Ambion Inc.) was all used as the reagent.

Template DNA and Reagents

Template DNA (XELF1-α), which was used in the present examples, was prepared in the following manner.

Control DNApTRI-Xef1 in an in vitro transcription reaction kit (MEGAscript T3 kit, Ambion Inc.) was treated with EcoRI restriction enzyme and about 1.8 kb XELF1-αDNA was sliced off. This DNA fragment was cloned into pBlue-script II (available from Toyobo Co. Ltd., manufactured by Stratagene Inc.) to obtain DNA of pBlue-XELF 1-α (about 4.76 kb). The DNA of pBlue·XELF1-α was treated with SmaI restriction enzyme to produce linear DNA, which was used in the in vitro transcription reaction. NTP, 10× Transcription buffer, and T3 RNA polymerase, which were used in the in vitro transcription reaction, were the reagents from a MEGAscript T3 kit (Ambion Inc.) for use.

Probe Syntheses (a) Probes having a base sequence complementary to that in the vicinity of the 5'-terminus of the RNA:

XELF-1F donor probe, 5'-BODIPY493/503-AGCCTTTTCCCATCTC-3' (SEQ ID NO: 1), is complementary to the base sequence, base sequence Nos. 184–199 of XELF-α (GeneBank Accession No. M25504), and it has a BODIPY493/503 dye bound to its 5'-terminus, A.

XELF-1F acceptor probe, 5'-AGGCATACTTG (Cy5) AAGG-3' (SEQ ID NO: 2), is complementary to the base sequence, base sequence Nos. 200–214 of XELF-α, and it has a Cy5 dye bound to the above-mentioned position (between "G" and "A").

(b) Probes having a base sequence complementary to that in the intermediate part of the RNA:

XELF-2F donor probe, 5 '-BODIPY493/503-TCTTGATGTATGTGC-3' (SEQ ID NO: 3), is complementary to the base sequence, base sequence Nos. 566–580 of XELF1-α, and it has a 5'-BODIPY493/503 dye bound to its 5'-terminus, T.

XELF-2F acceptor probe, 5'-GGTTGTAACCA (Cy5) ATCT-3' (SEQ ID NO: 4), is complementary to the base sequence, base sequence Nos. 581–595 of XELF-α, and it has a Cy5 dye bound to the above-mentioned position (between "A" and "A").

(c) Probes having a base sequence complementary to that in the vicinity of the 3'-terminus of the RNA:

XELF-3F donor probe, 5'-BODIPY493/503-TTAAACTCTGATGGCC-3' (SEQ ID NO: 5), is complementary to the base sequence, base sequence Nos. 1504–1519 of XELF-α, and it has a 5'-BODIPY493/503 dye bound to its 5'-terminus, T.

XELF-3F acceptor probe, 5'-ACCAGTCTTTT (Cy5) ACTA-3' (SEQ ID NO: 6), is complementary to the base sequence, base sequence Nos. 1520–1534 of XELF-α, and it has a Cy5 dye bound to the above-mentioned position (between "T" and "A").

(d) Probes expected to be unlikely to hybridize to the RNA:

XELF-4F donor probe, 5'-BODIPY493/503-AGTACCAGTGATCAT-3' (SEQ ID NO: 7), is complementary to the base sequence, base sequence Nos. 346–360 of XELF-α, and it has a 5'-BODIPY493/503 dye bound to its 5'-terminus, A.

XELF-4F acceptor probe, 5'-ACAGTCAGCCT (Cy5) GAGA-3' (SEQ ID NO: 8), is complementary to the base sequence, base sequence Nos. 361–375 XELF-α, and it has a Cy5 dye bound to the above-mentioned position (between "T" and "G").

(e) C-FOS donor probe/C-FOS acceptor probe:

C-FOS donor probe, 5'-BODIPY493/503-TCTAGTTGGTCTGTC-3' (SEQ ID NO: 9), is complementary to the base sequence, base sequence Nos. 662–676 of c-fos RNA, and it has a 5'-BODIPY493/503 dye bound to its 5'-terminus, A.

C-FOS acceptor probe, 5'-GCAGACTTCTC (Cy5) ATCT-3' (SEQ ID NO: 10), is complementary to the base sequence, base sequence Nos. 677–691 of c-fos, and it has a Cy5 dye bound to the above-mentioned position (between "C" and "A").

(f) XELF-5F probe:

XELF-5F acceptor probe, 5'-ACCCAGGCATACTTG (Cy5) -3' (SEQ ID NO: 11), is complementary to the base sequence, base sequence Nos. 204–218 of XELF1-αRNA, and it has a Cy5 dye bound to its 3'-terminus, G.

According to the β-cyanoethylamidite method, the synthesis of the probes described above was conducted using an automated synthesizer (Model 1394, Perkin Elmer Inc. or Expedite Model 18909, Perspective Inc.). The resulting crude product was analyzed with a DEAE-HPLC and the main component was fractionated. Its retention time was 20–30 min. Further, the fractionated solution was lyophilized after desalting.

The DEAE-HPLC (anion-exchange) conditions are as follows:

Solvent A: 0.2 M HCOONH$_4$ 20% CH$_3$CN;
Solvent B: 1.0 M HCOONH$_4$ 20% CH$_3$CN;
Column: TSK-gelDEAE-2WS 4.6×250 mm (available from Tosoh Co. Ltd.);
Flow rate: 0.8 ml/min;
Temperature: 40° C.; and
B gradient: 35–85% (20 min).

Fluorescence-Labeling Reaction with Cy5 Dye

For modification of the 5'-termini of probes, or for use at the intermediate positions of probes, 6-(trifluoroacetylamino)hexyl-(2-cyanoethyl)-N,N-diisopropyl)-phosphoroamidite (TFAc-hexanolamine linker, available from Perkin Elmer Japan Co. Ltd., Cat No. 400808) and Uni-Link AminoModifier (available from Clonetech Laboratories, Inc., Code No. CL5190-1; loc. cit.) were used, respectively, together with the automated synthesizers described above.

The solidly dried oligonucleotide as obtained above was dissolved in 200 μl of 0.5 M NaHCO$_3$/NaHCO$_3$ buffer (pH 9.0) and the Cy dye was dissolved in sterilized water. Both were mixed and allowed to react overnight under the shielded light. The reaction solution was gel-filtrated to remove unreacted dye. Analysis was performed on an RP-HPLC (B gradient: 15–65%, 20 min), and the component of the peak at around 20–25 min was fractionated. Spectrophotometer confirmed the presence of absorption at 260 nm, as well as the presence of the absorption of the fluorescent dye.

The RP-HPLC (reverse phase C 18) conditions are as follows:

Solvent A: 0.05 M TEAA 5% CH$_3$CN;
Solvent B: 0.05 M TEAA 40% CH$_3$CN;
Column: CAPCELL PAKC18 6×250 mm (available from Shiseido Co. Ltd.);
Flow rate: 1.0 ml/min; and
Temperature: 40° C.

Fluorescence-Labeling
Reaction with BODIPY493/503 Dye

For modification of the 5'-termini of probes or for use at the intermediate positions of probes, 6-(trifluoroacetylamino)hexyl-(2-cyanoethyl)-N,N-diisopropyl)-phosphoroamidite (TFAc-hexanolamine linker) and Uni-Link AminoModifier were used, respectively, together with the automated synthesizers described above.

NHSS 2.5 mg was dissolved in 30 μl of sterilized water and EDAC 5 mg in 50 μl of sterilized water, respectively. To this was mixed 1 mg of BODIPY propionic acid dissolved in 50 μl of DMF, and it was allowed to react at room temperature for 30 min. The resulting solution was mixed with the solidly dried oligonucleotide dissolved in 300 μl of 0.5 M NaHCO$_3$/NaHCO$_3$ buffer (pH 9.0), and it was allowed to react overnight under the shielded light. The reaction solution was gel-filtrated to remove unreacted dye.

Analysis was performed on an RP-HPLC (FITC, B gradient: 30–80%, 20 min), and the peak at around 25–35 min was fractionated. Spectrophotometer confirmed the presence of absorption at 260 nm, as well as the presence of the absorption of the fluorescent dye. These were lyophilized and stored.

Transcription Reaction

Reaction conditions for the in vitro transcription reaction to be monitored in this invention are not particularly limited, and are changeable according to the in vitro transcription reactions employed.

Fluorescence Spectrum Measurements

A spectrofluorometer (F4500 type available from Hitachi Co. Ltd.) was employed. The measurement of fluorescence spectra was performed in the range of from 500 to 750 nm by excitation at 480 nm; and the ratio of the fluorescence intensity of acceptor to that of donor was calculated, which was termed as the relative fluorescence intensity (Ia/Id).

Example 1

Correlation between Changes in Fluorescence Spectra and the Quantities of Synthesized RNA According to the methods of this invention, to confirm that the fluorescence spectrum changes as RNA is synthesized by an in vitro transcription reaction for RNA synthesis, the following experiment was conducted. To 150 μl of a transcription reaction solution having the composition as described below was added a pair of fluorescence-labeled probes of two types and the transcription reaction for RNA synthesis was carried out. The pair of probes of two types (XELF-1F donor probe/ XELF-1F acceptor probe), which had a base sequence complementary to the vicinity of the 5'-terminus of the RNA, was used. Reaction was initiated by the addition of template DNA. The reaction was conducted at 37° C.

(Composition of the Transcription Reaction Solution)

| | |
|---|---|
| ATP, GTP, CTP, and UTP | each 75 mM |
| XELF1-αDNA | 6 pmol |
| 10 × Transcription buffer | 15 μl |
| XELF-1F (donor probe) | 2578 pmol |
| XELF-1F (acceptor probe) | 2577 pmol |
| T3 RNA polymerase | 15 μl |

Totaled to 150 μl with water treated with diethyl pyrocarbonate (DEPEC).

Figure 9:
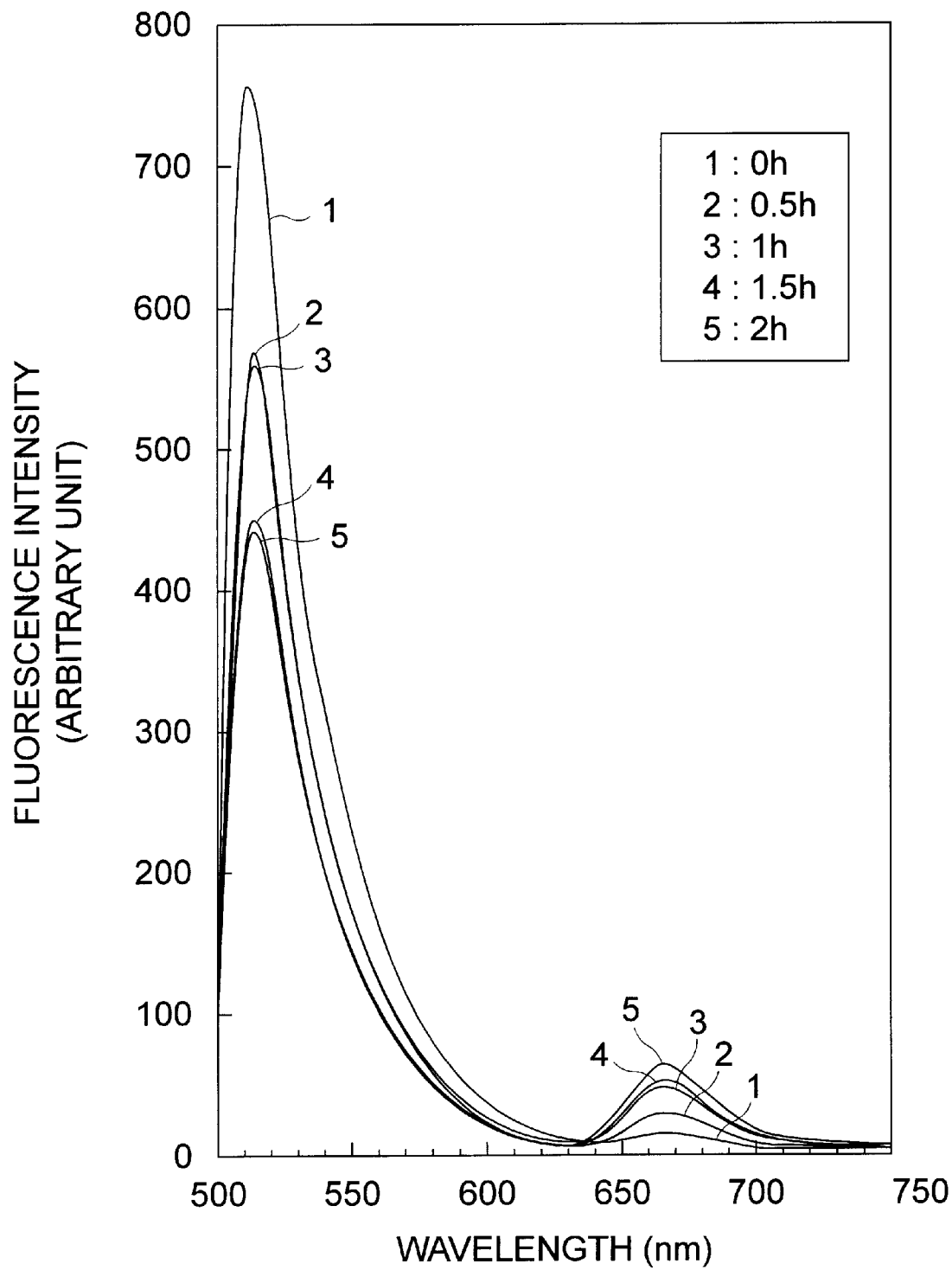
FIG. 9 is a plot showing that the fluorescence spectrum changes with the time-dependent change of the in vitro transcription reaction, following the monitoring method according to the invention.

Aliquots (each 5 μl) of the reaction solution were fractionated at the predetermined intervals, to which was added 145 μl of 1× SSC containing 20 mM EDTA. Subsequently, the measurement of fluorescence spectra was performed. In the fluorescence spectra, the fluorescence resulting from Bodipy493/503 of the donor probe was observed at around 520 nm, and that resulting from the acceptor probe at around 670 nm. With the passage of reaction time, the fluorescence resulting from Bodipy493/503 decreased and that resulting from Cy5 increased (FIG. 9). When a pair of probes of two types (C-FOS donor probe/C-FOS acceptor probe) having no base sequence complementary to XELF1-αRNA was used instead of the XELF-1F donor probe/ XELF-1F acceptor probe in a control experiment, no change was observed in its fluorescence spectrum. Namely, an observable change in the fluorescence spectrum arises from that the probes added to the transcription reaction solution are specifically hybridized to specified sites of the synthesized RNA. The ratios (Ia/Id) of the fluorescence intensities at 520 nm (Id) to those at 670 nm (Ia) were plotted against reaction time, which is shown in FIG. 10B.

The quantities of the synthesized RNA on these occasions were also determined according the following procedure. Aliquots (each 5 μl) were fractionated from the reaction solution at the predetermined intervals. To this was added 145 μl of a quenching solution (a mixed solution of 15 μl of 5 M NH$_4$OAc, 100 mM EDTA, and 130 μl of water treated with diethyl pyrocarbonate (DEPEC)), and thus reaction was terminated. Subsequently, phenol-chloroform extraction and chloroform extraction was conducted, and RNA was recovered by precipitation with isopropyl alcohol. After the recovered RNA precipitates were dissolved in 20 μl of the DEPEC-treated water, the quantities of the RNA were determined by absorbance at 260 nm. The quantities of the RNA were plotted against reaction time, which is shown in FIG. 10A.

Figure 10A:
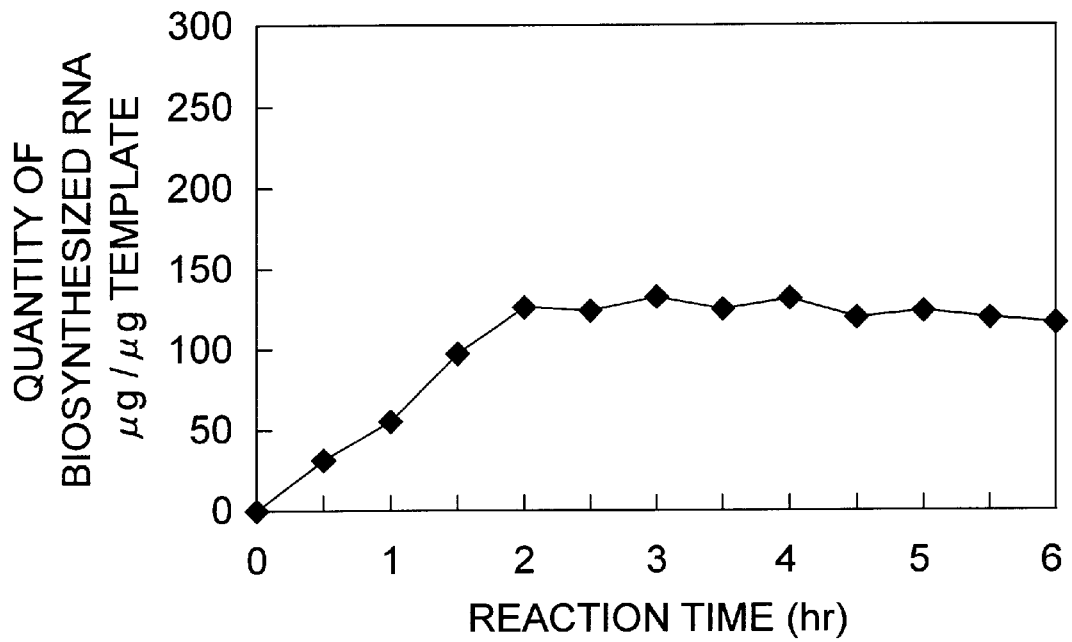
FIG. 10A is a plot showing that the time-dependent change of the in vitro transcription reaction can be measured as the time-dependent change of a fluorescence spectrum, following the monitoring method according to the invention, where the time-dependent change of the quantity of transcribed, synthesized RNA that is determined from OD 260 values after extraction of the synthesized RNA is indicated.
Figure 10B:
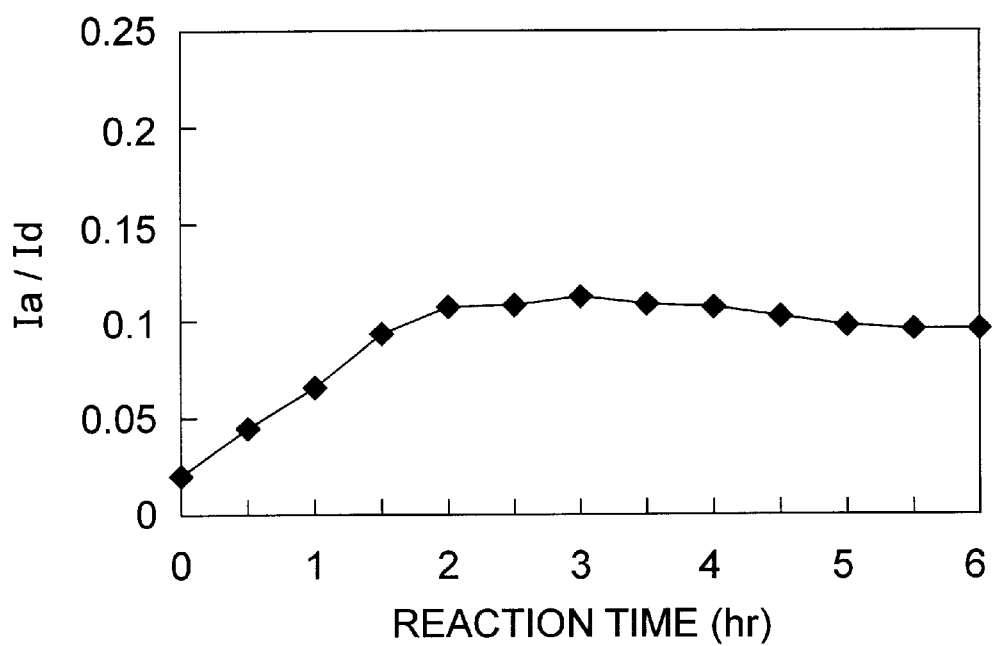
FIG. 10B is a plot showing that the time-dependent change of the in vitro transcription reaction can be measured as the time-dependent change of a fluorescence spectrum, following the monitoring method according to the invention, where the time-dependent change of the ratio of fluorescence intensities at two wavelengths (Ia/Id: Id is the fluorescence intensity at 515 nm and Ia is the fluorescence intensity at 670 nm) on the fluorescence spectrum is indicated. Likewise are the ordinates in FIGS. 11, 14 and 17.

A comparison between FIG. 10A and FIG. 10B reveals that the change in the fluorescence spectrum and the change in the quantities of the synthesized RNA shows a good correlation.

Example 2
Monitoring of Transcription Reaction by Three Pairs of Probes Differing in Their Hybridization Sites on RNA The monitoring of a transcription reaction for RNA synthesis according to the present methods does not depend on the sites on RNA to which the probes for use hybridize. An oligonucleotide having a base sequence complementary to the vicinity of the 5'-terminus (184–214) of the RNA was used as the probe in Example 1. Even if oligonucleotides having base sequences complementary to other sites on the RNA were used as probes, monitoring of the RNA transcription reaction would be likewise possible: To confirm this an XELF-2F probe having a base sequence complementary to the intermediate region (566–595) of the RNA and an XELF-3F probe having a base sequence complementary to the vicinity of the 3'-terminus (1504–1534) of the RNA were prepared.

The three pairs of probes (XELF-1F probes, XELF-2F probes, and XELF-3F probes) were added to transcription reaction solutions, respectively to prepare three pairs of samples, which were subjected to the transcription reaction for RNA synthesis.
(Compositions of the Transcription Reaction Solutions)
Sample 1: XELF-1F probes

| ATP, GTP, CTP, and UTP | each 75 mM |
|---|---|
| XELF1-αDNA | 0.8 pmol |
| 10 × Transcription buffer | 5 μl |
| XELF-1F donor probe | 430 pmol |
| XELF-1F acceptor probe | 430 pmol |
| T3 RNA polymerase | 5 μl |

Totaled to 50 μl with DEPEC-treated water.

| ATP, GTP, CTP, and UTP | each 75 mM |
|---|---|
| XELF1-αDNA | 0.8 pmol |
| 10 × Transcription buffer | 5 μl |
| XELF-2F donor probe | 430 pmol |
| XELF-2F acceptor probe | 430 pmol |
| T3 RNA polymerase | 5 μl |

Totaled to 50μl with the DEPEC-treated water.

Sample 3: XELF-3F probes

| ATP, GTP, CTP, and UTP | each 75 mM |
|---|---|
| XELF1-αDNA | 0.8 pmol |
| 10 × Transcription buffer | 5 μl |
| XELF-3F donor probe | 430 pmol |
| XELF-3F acceptor probe | 430 pmol |
| T3 RNA polymerase | 5 μl |

Totaled to 50 μl with the DEPEC-treated water.

Figure 11:
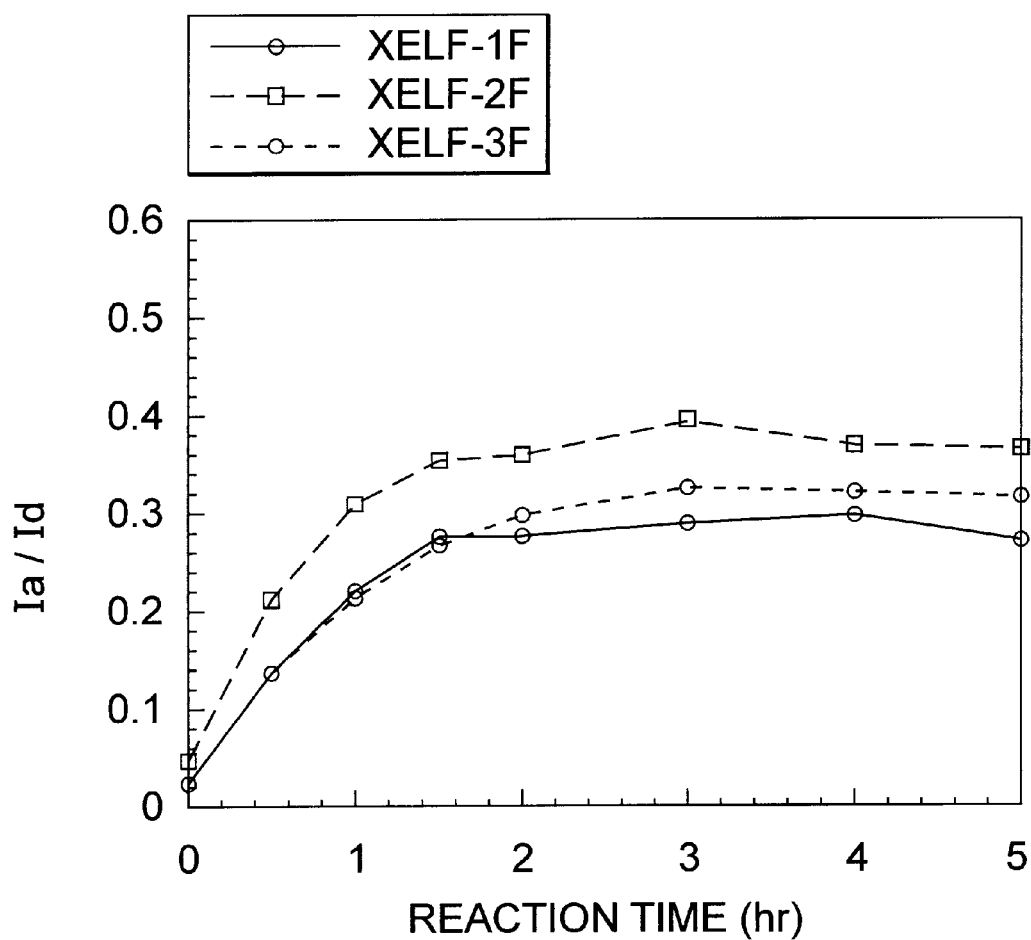
FIG. 11 shows the time-dependent changes of the ratio of fluorescence intensities at two wavelengths (Ia/Id) on the fluorescence spectra when three pairs of probes having different sites on RNA for hybridization were respectively used to monitor the transcription reaction for RNA synthesis: It is shown that the monitoring of transcription reactions for RNA synthesis according to the present method does not rely on the hybridization sites on RNA of the probes to be used.

For the respective samples, the ratios of fluorescence intensities at the two wavelengths of their fluorescence spectra (Ia/Id) were plotted against reaction time, which is shown in FIG. 11. Time-dependent changes in the fluorescence spectra of the three samples show similar characteristics. It is thus shown that the monitoring of a transcription reaction for RNA synthesis according to the present methods does not depend on the hybridization sites on RNA by the probes to be used.

Example 3
Monitoring of the Biosynthesis of Full-Length RNA by In Vitro Transcription Reaction Transcription reaction by the use of template DNA obtainable by deletion of its 3'-termninus from XELF1-α and that by the use of full-length template DNA were monitored by probes having a base sequence complementary to the vicinity of the 3'-terminus and those having a base sequence complementary to the 5'-terminus, respectively. Then time-dependent changes in the fluorescence spectra were observed.
(Composition of the Transcription Reaction Solutions)

| ATP, GTP, CTP, and UTP | each 75 mM |
|---|---|
| 10 × Transcription buffer | 7 μl |
| XELF-3F donor probe | 608 pmol |
| XELF-3F acceptor probe | 608 pmol |
| T3 RNA polymerase | 7 μl |

To the reaction solution described above was added each 3.5 jig of template DNA obtainable by deletion of 1020 bases from its 3'-terminus of XELF1-α and full-length template DNA of XELF1-α, respectively; and then, the solution was totaled to 70 μl with the DEPEC-treated water and allowed to react at 37° C.

Figure 12A:
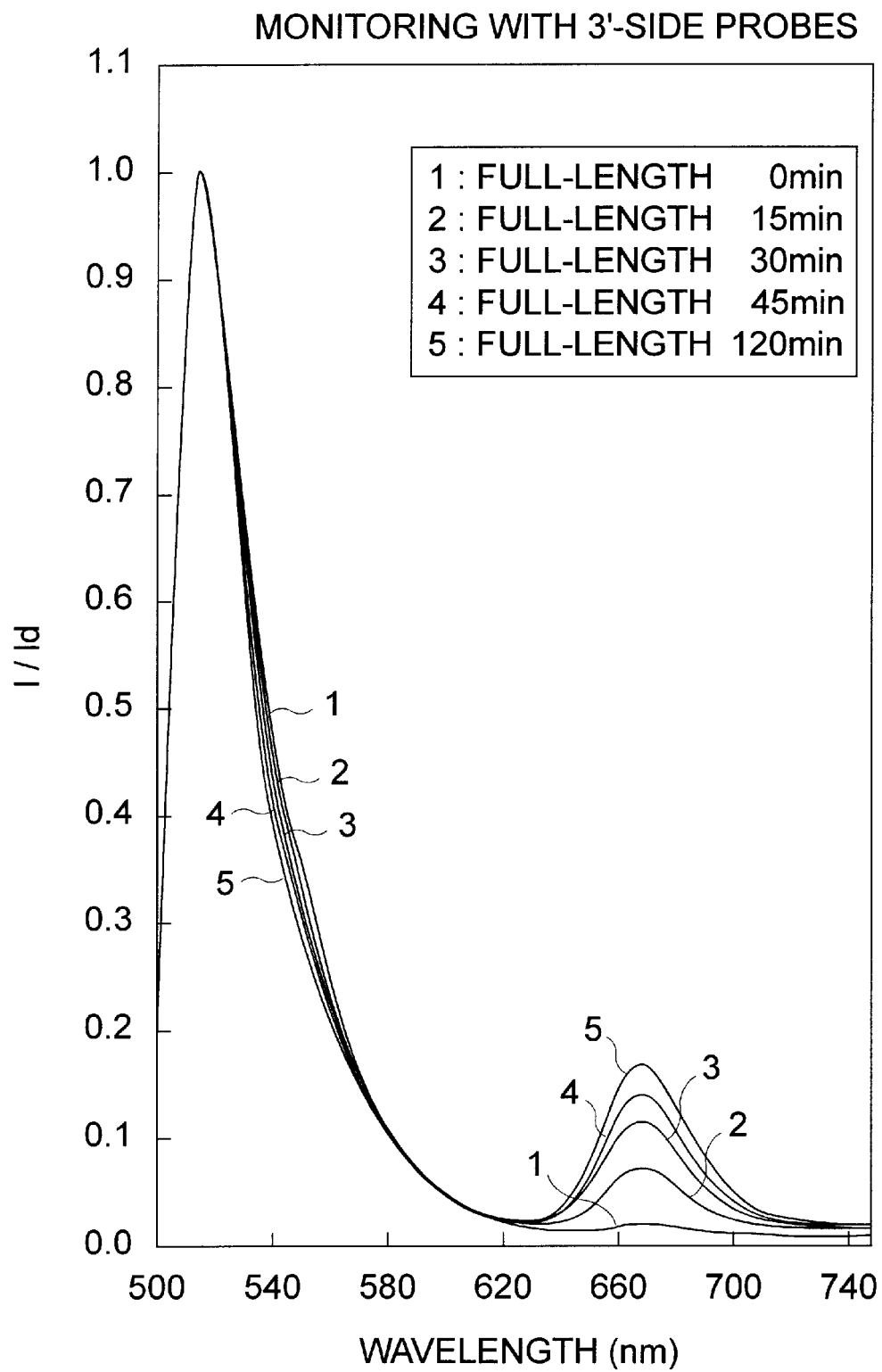
FIG. 12A is a plot showing the results obtained when full-length DNA of XELF-α was utilized as a template and XELF-3F probes, which hybridize to the vicinity of the 3'-terminus, were added to a transcription reaction solution and the time-dependent change of its fluorescence spectrum was measured. The ordinate I/Id represents fluorescence intensities normalized with the fluorescence intensity (Id) at 515 nm. Likewise are the ordinates in FIGS. 12B, 13A, 13B, 15A, 15B, 18A, 18B, and 18C.
Figure 12B:
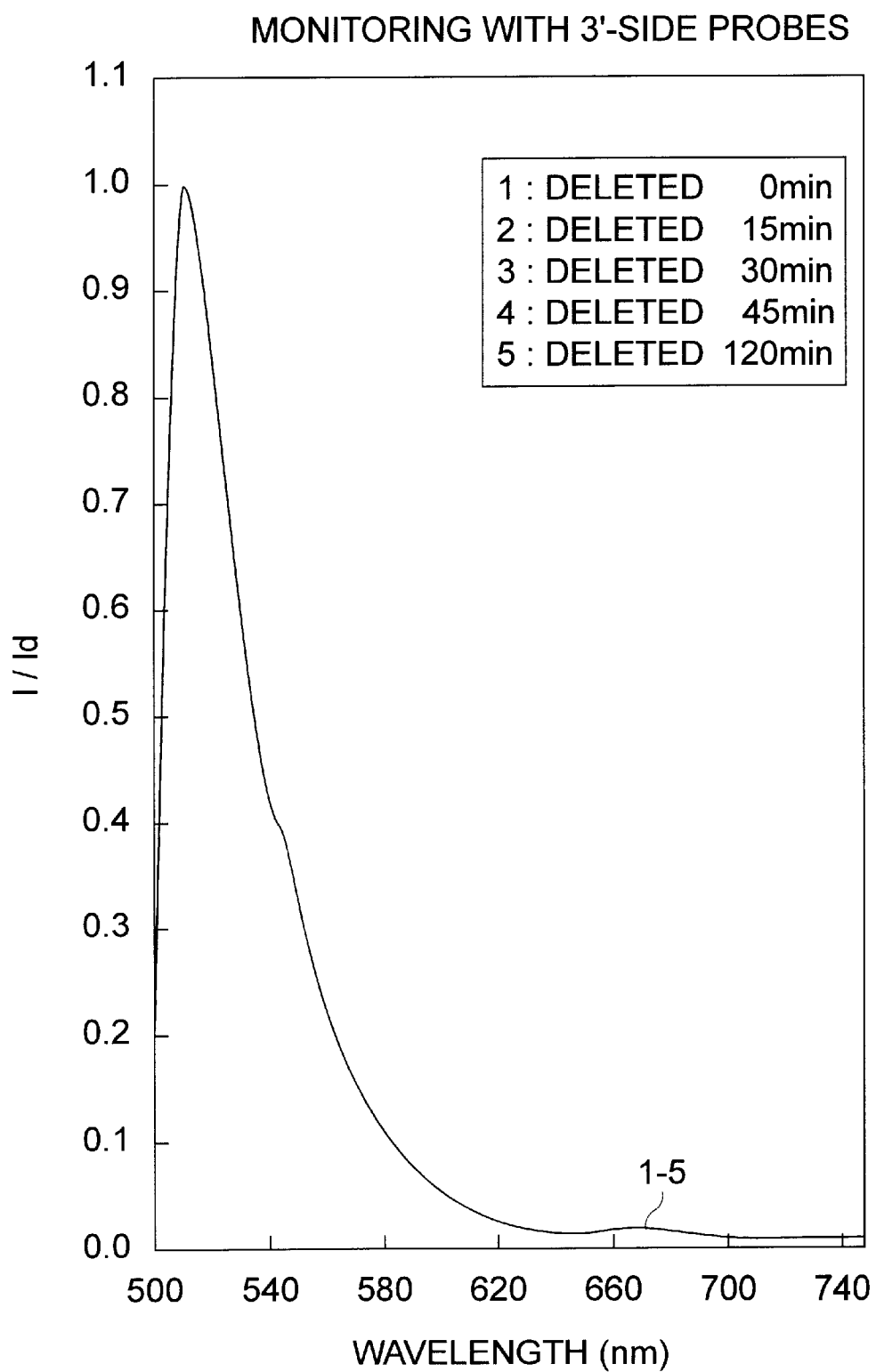
FIG. 12B is a plot showing the results obtained when DNA of XELF-α having a deletion of the 3'-terminus was utilized as a template and XELF-3F probes, which hybridize to the vicinity of the 3'-terminus, were added to a transcription reaction solution and the time-dependent change of its fluorescence spectrum was measured.

The two kinds of DNA, namely XELF1-α the 3'-terminus of which had been deleted and the fall-length XELF1-α, were respectively used as templates, and the XELF-3F donor probe and XELF-3F acceptor probe, both of which hybridize to the vicinity of the 3'-terminus, were added; and time-dependent changes in their fluorescence spectra were measured. The results are shown in FIGS. 12A and 12B.

Where the XELF-3F donor probe and XELF-3F acceptor probe, both of which hybridize to the vicinity of the 3'-terminus, were used with the deleted DNA as the template to measure the time-dependent change, no change in the fluorescence spectrum was observed (FIG. 12B); whereas, the time-dependent change in the fluorescence spectrum was observed where the full-length DNA was used as the template (FIG. 12A).

Figure 13A:
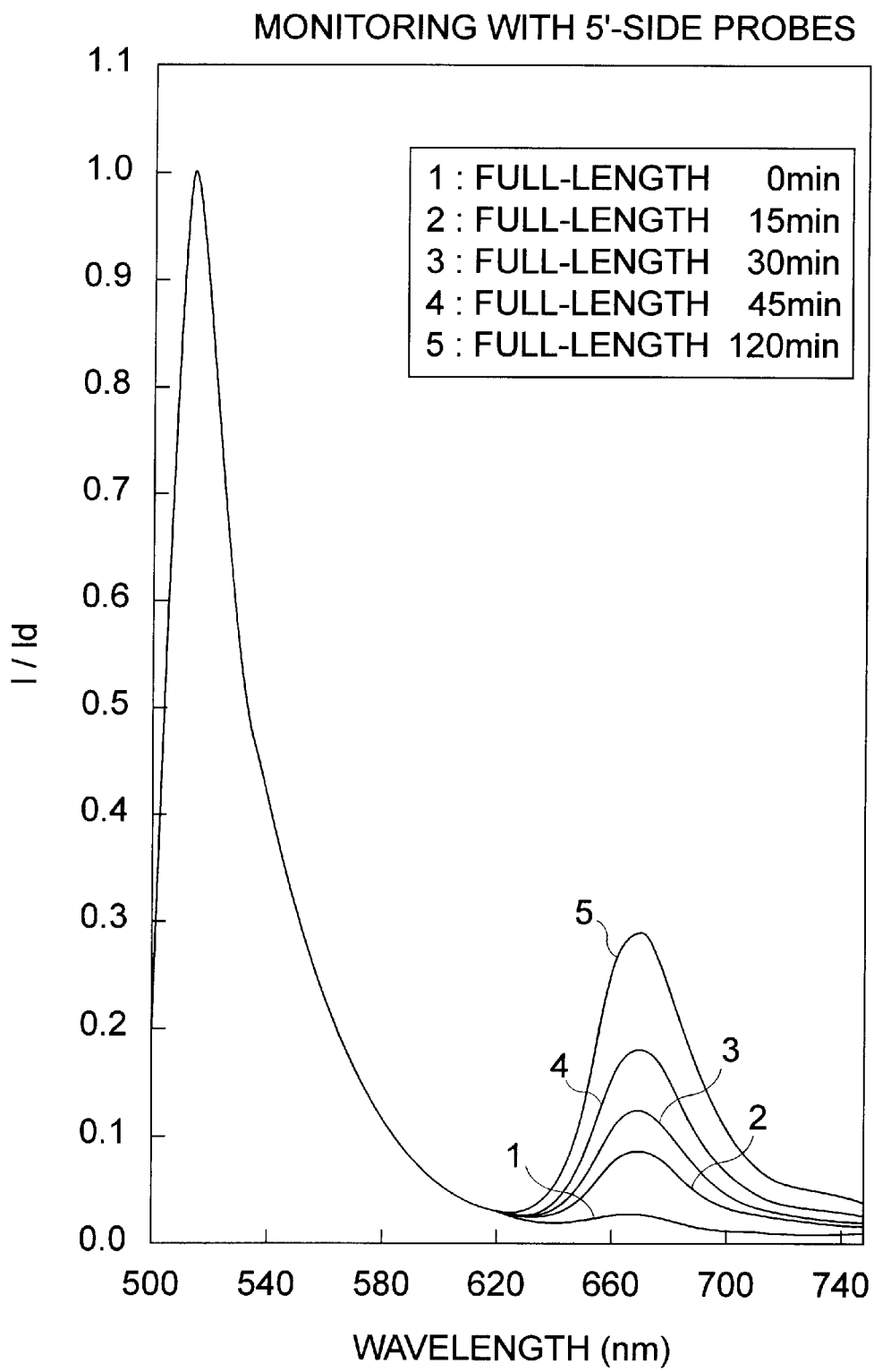
FIG. 13A is a plot showing the results obtained when the full-length DNA of XELF-α was utilized as a template and XELF-1F probes, which hybridize to the vicinity of the 5'-terminus, were added to a transcription reaction solution and the time-dependent change of its fluorescence spectrum was measured.
Figure 13B:
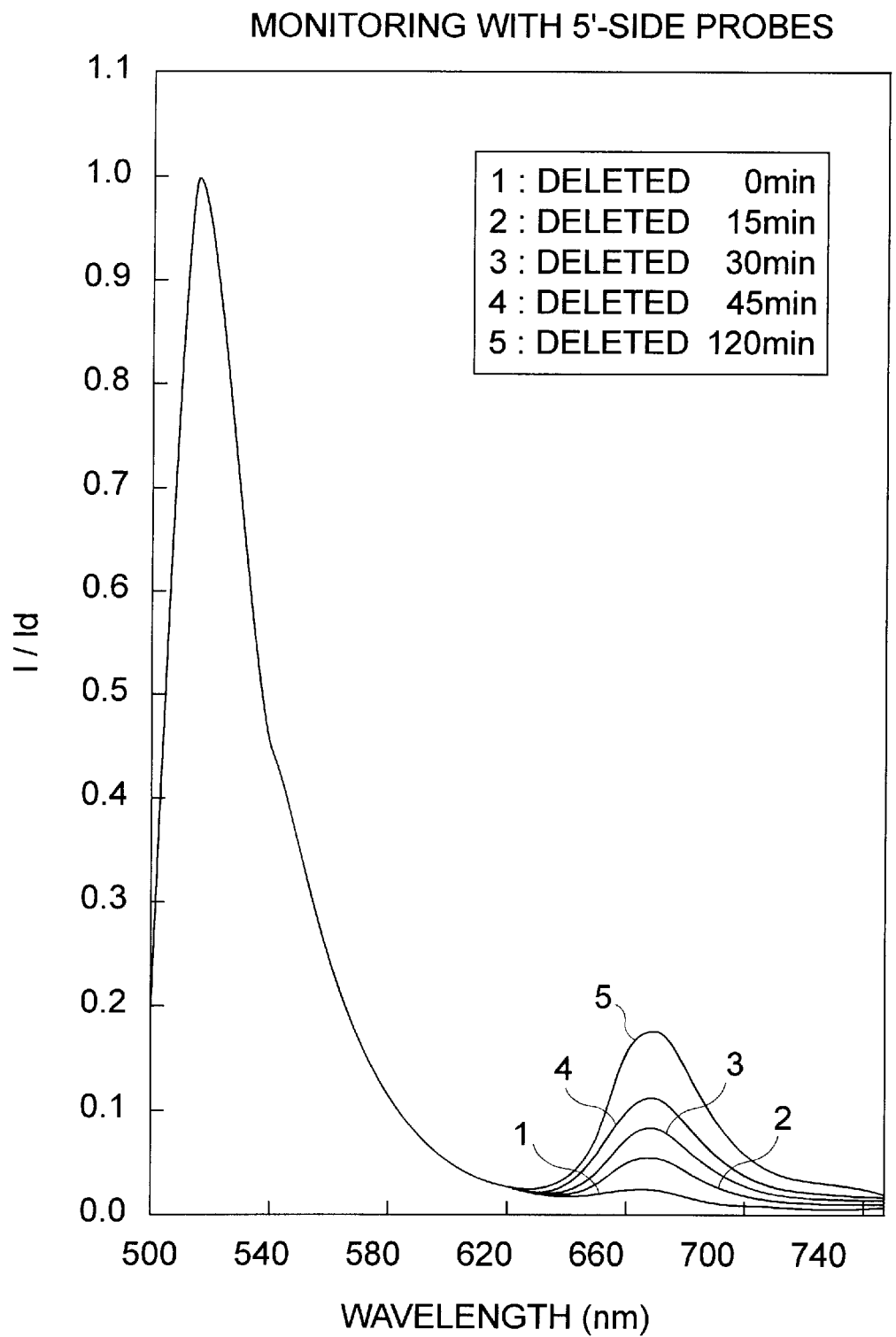
FIG. 13B is a plot showing the results obtained when the DNA of XELF-α having a deletion of the 3'-terminus was utilized as a template and the XELF-1F probes, which hybridize to the vicinity of the 5'-terminus, were added to a transcription reaction solution and the time-dependent change of its fluorescence spectrum was measured.

On the other hand, the XELF-1F donor probe and XELF-1F acceptor probe, both of which hybridize to the vicinity of the 5'-terminus, were used to measure the time-dependent changes in the fluorescence spectra. The results are shown in FIGS. 13A and 13B. For each of the deleted and the full-length templates, the time-dependent change in the fluorescence spectrum was observed.

To confirm the length of biosynthesized RNA, 1 μl of DNase I (2U/μl) was added to each 20 μl of the respective reaction solutions after reaction, and allowed to react at 37° C. for 30 min. Subsequently, phenol-chloroform extraction and chloroform extraction was conducted, and the biosynthesized RNA was recovered by precipitation with isopropyl alcohol. The recovered RNA precipitates were dissolved in 20 μl of the DEPEC-treated water, and the sizes of the RNA were determined by agarose gel electrophoresis. Where the full-length template was used, full-length RNA (ca. 1.9 kb) was synthesized; whereas, RNA having a deletion of about 1 kb was synthesized in the case of the deleted template DNA.

The above results suggest the following: to monitor the biosynthesis of the full-length (having the desired length) RNA, the probes, which are complementary to the vicinity of the 3'-terminus of the RNA to be biosynthesized, may be added to the transcription reaction solution and the time-dependent change in the fluorescence spectrum may be observed.

Example 4
Quantitation of RNA Biosynthesis through the Monitoring of In Vitro Transcription The concentrations of the biosynthesized RNA are plotted against the ratio (Ia/Id) of the fluorescence intensity of donor to that of acceptor, which is obtained from the fluorescence spectra, to prepare a calibration curve; and this will enable the quantity of the RNA (concentration) to be known.
(Preparation of the Calibration Curve)

To the transcription reaction solution as described below were added 2.5 gg of template DNA of XELF1-α and XELF-1F probes in a molar ratio of 1000 based on the template DNA. After the solution was totaled to 50 μl with DEPEC-treated water, it was allowed to react at 37° C. Aliquots (each 2.5 μl) of reaction solution were collected from this transcription reaction solution at the predetermined intervals for purposes of the measurement of fluorescence spectra and the RNA extraction.
(Composition of the Transcription reaction Solution)

| ATP, GTP, CTP, and UTP | each 75 mM |
| XELF1-αDNA | 0.8 pmol |
| 10 × Transcription buffer | 5 μl |
| XELF-1F donor probe | 820 pmol |
| XELF-1F acceptor probe | 820 pmol |
| T3 RNA polymerase | 5 μl |

Totaled to 50 μl with the DEPEC-treated water.

The fluorescence measurements were performed after dilution with 1× SSC containing 147.5 μl of 20 mM EDTA. The quantities of the biosynthesized RNA were calculated from the absorbance values at 260 nm obtained by the RNA extraction from the transcription solutions, which were fractionated at the predetermined intervals, according to a similar method to Example 1. In the quantitation by the 260-nm absorbance, values that include unreacted ribonucleotides or template DNA present in the reaction solutions may also have been quantitated. To correct this effect, the absorbance at 260 nm of a sample solution prior to the RNA biosynthesis was quantitated through similar extraction manipulations, and a calibration curve was prepared using the result obtainable by subtracting this value from each determined value.

Figure 14:
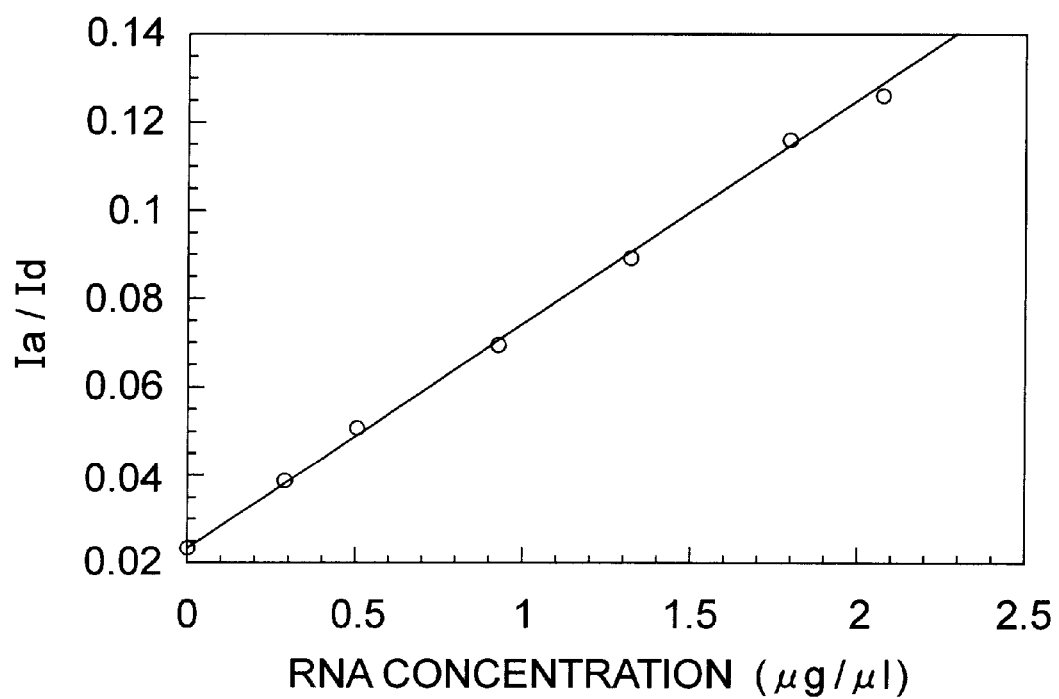
FIG. 14 is a plot showing a calibration curve prepared in Example 4.

FIG. 14 shows the calibration curve obtained by the above-mentioned method. This calibration curve corresponds to the case where a 1000-fold quantity of the probes in a molar ratio was added to the template DNA. The actual quantitation determines the ratios of fluorescence intensities (Ia/Id) from changes in fluorescence spectra and calculates the concentrations of the biosynthesized RNA based on the calibration curve as described previously.

If the calibration curves that correspond to the added amounts of probes are prepared in advance, it will be possible to find the quantities of the biosynthesized RNA on real-time while monitoring fluorescence spectra.

Example 5
Simultaneous Monitoring of the Initiation of In Vitro Transcription Reaction and Full-Length RNA If two or more pairs of fluorescence-labeled probes are used simultaneously, it is possible to simultaneously confirm the initiation of an in vitro transcription reaction, as well as the manner in which full-length (the desired length) RNA is being synthesized.

One pair, which is probes that hybridize to the vicinity of the 5'-terminus, is intended for monitoring the initiation of the transcription reaction, while the other pair, which is probes that hybridize to the vicinity of the 3'-terminus, is intended for monitoring as to whether the full-length RNA is biosynthesized. The one pair of probes of two types that hybridize to the 5'-terminus were labeled with the combination of BODIPY493/503 and XRITC, and the other pair of probes of two types that hybridize to the 3'-terminus labeled with the combination of BODIPY493/503 and Cy5.
(Probes Used in the Monitoring)

Probes that hybridize to the 5'-terminus:
XELF-1F donor probe 5'-BODIPY493/503-AGCCTTTTCCCATCTC-3 (SEQ ID NO: 1)
XELF-1F acceptor probe (5 '-AGGCATACTTG(XRITC) AAGG)3 (SEQ ID NO: 2)
Probes that hybridize to the 3'-terminus:
XELF-3F donor probe (5'-BODIPY493/503-TTAAACTCTGATGGCC) 3(SEQ ID NO: 5)
XELF-3F acceptor probe (5'-ACCAGTCTTTT(Cy5) ACTA) 3' (SEQ ID NO: 6)

Two kinds of transcription reaction solution, to which full-length template DNA and template DNA having a deletion of the 3'-terminus were added respectively, were prepared in the following manner.
(Compositions of the Transcription Reaction Solutions)

Where the template DNA having a deletion of the 3'-terminus was added:

| ATP, GTP, CTP, and UTP | each 75 mM |
| XELF1-αDNA (deleted) | 1 pmol |
| 10 × Transcription buffer | 5 μl |
| XELF-1F donor probe | 820 pmol |
| XELF-1F acceptor probe | 820 pmol |
| XELF-3F donor probe | 820 pmol |
| XELF-3F acceptor probe | 820 pmol |
| T3 RNA polymerase | 5 μl |

Totaled to 50 μl with DEPEC-treated water.
Where the full-length template DNA was added:

| ATP, GTP, CTP, and UTP | each 75 mM |
| XELF1-αDNA (full length) | 0.8 pmol |
| 10 × Transcription buffer | 5 μl |
| XELF-1F donor probe | 820 pmol |

| | |
|---|---|
| XELF-1F acceptor probe | 820 pmol |
| XELF-3F donor probe | 820 pmol |
| XELF-3F acceptor probe | 820 pmol |
| T3 RNA polymerase | 5 µl |

Totaled to 50 µl with the DEPEC-treated water.

Figure 15A:
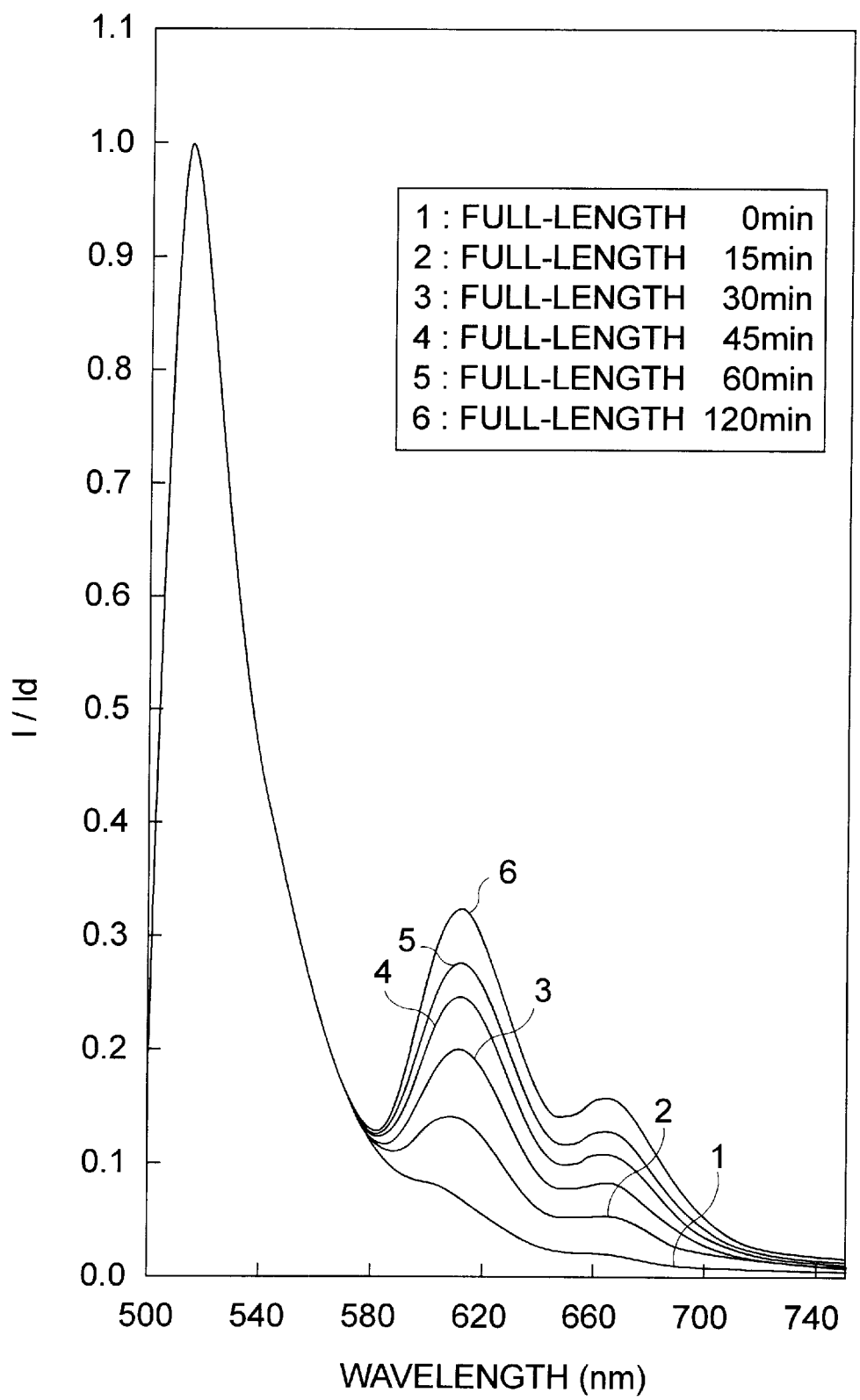
FIG. 15A is a plot showing the time-dependent change of the fluorescence spectrum where the full-length template DNA obtained in Example 5 was used.
Figure 15B:
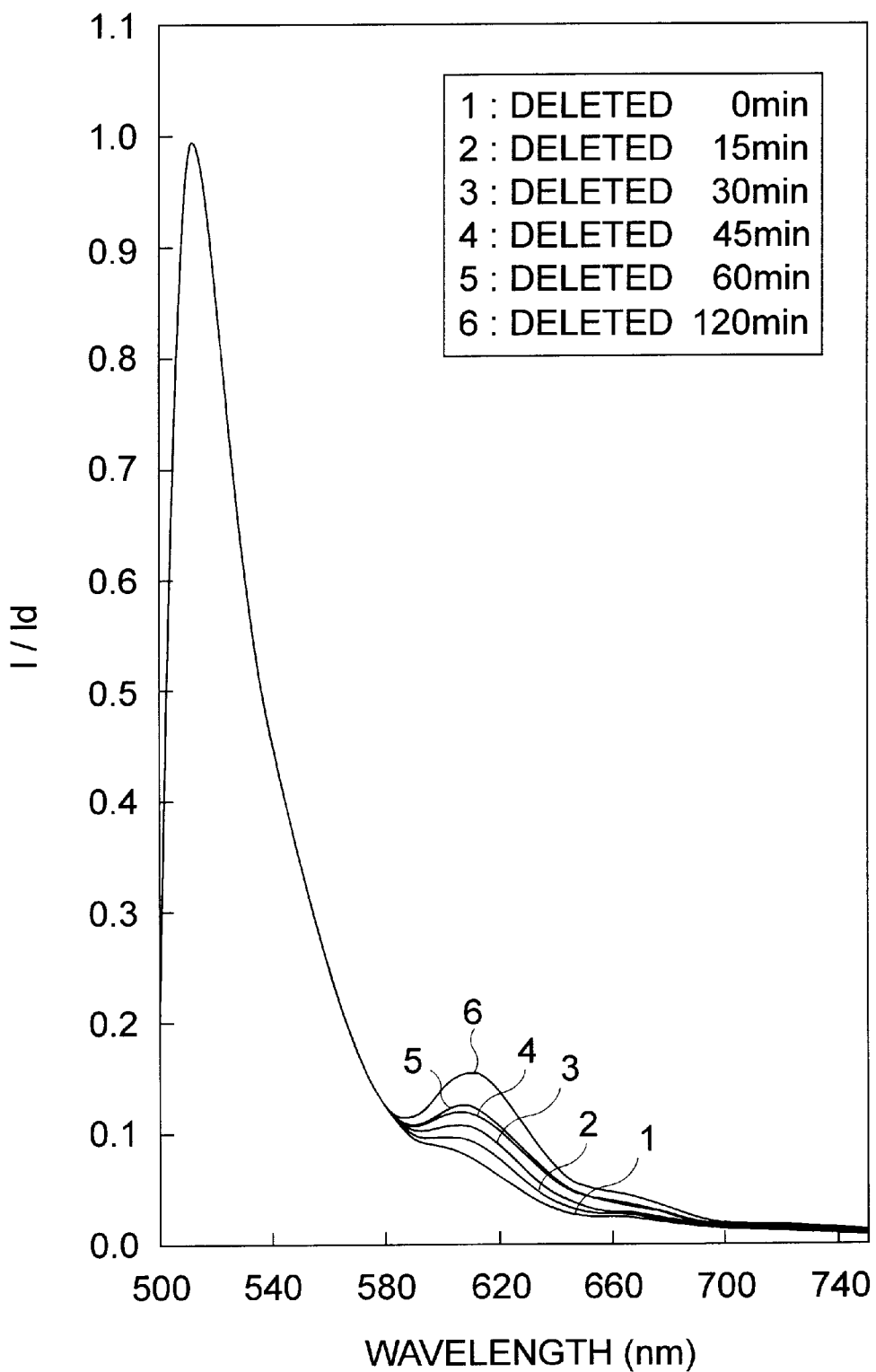
FIG. 15B is a plot showing the time-dependent change of the fluorescence spectrum where the deleted DNA template obtained in Example 5 was used.

FIG. 15A shows the time-dependent change in the fluorescence spectrum in the case where the full-length template DNA was used; whereas, FIG. 15B shows the time-dependent change in the fluorescence spectrum in the case where the deleted template DNA was used. In the fluorescence spectra of FIG. 15A, increases in the fluorescence of XRITC at around 610 nm and those in the fluorescence of Cy5 at around 670 nm were observed at the same time.

On the other hand, while increases in the fluorescence of XRITC at around 610 nm were observed, no changes in the fluorescence resulting from Cy5 were observed.

The foregoing results suggest that if two or more pairs of probes having an appropriate combination of fluorescent dyes are employed, it is possible to simultaneously monitor the initiation of a transcription reaction and the synthesis of full-length RNA.

Example 6

Monitoring of the Rate of In Vitro Transcription Reaction

Two pairs of the transcription reaction solutions differing in the added amounts of T3 polymerase were prepared as described below.

(Composition of the Transcription Reaction Solutions)

| | |
|---|---|
| ATP, GTP, CTP, and UTP | each 75 mM |
| XELF1-αDNA | 0.8 pmol |
| 10 × Transcription buffer | 5 µl |
| XELF-1F donor probe | 820 pmol |
| XELF-1F acceptor probe | 820 pmol |

Transcription reaction solutions, each 50 µl, were prepared by adding to the reaction solution as described above, 5 µl of T3 RNA polymerase (expressed as "normal" in FIG. 16) and 2.5 µl of T3 RNA polymerase (expressed as "½" in FIG. 16), respectively. The ratios of fluorescence intensities (Ia/Id), which were determined from the fluorescence spectra, were converted to RNA concentrations using the calibration curve as described previously, and they were plotted against reaction time.

Figure 16:
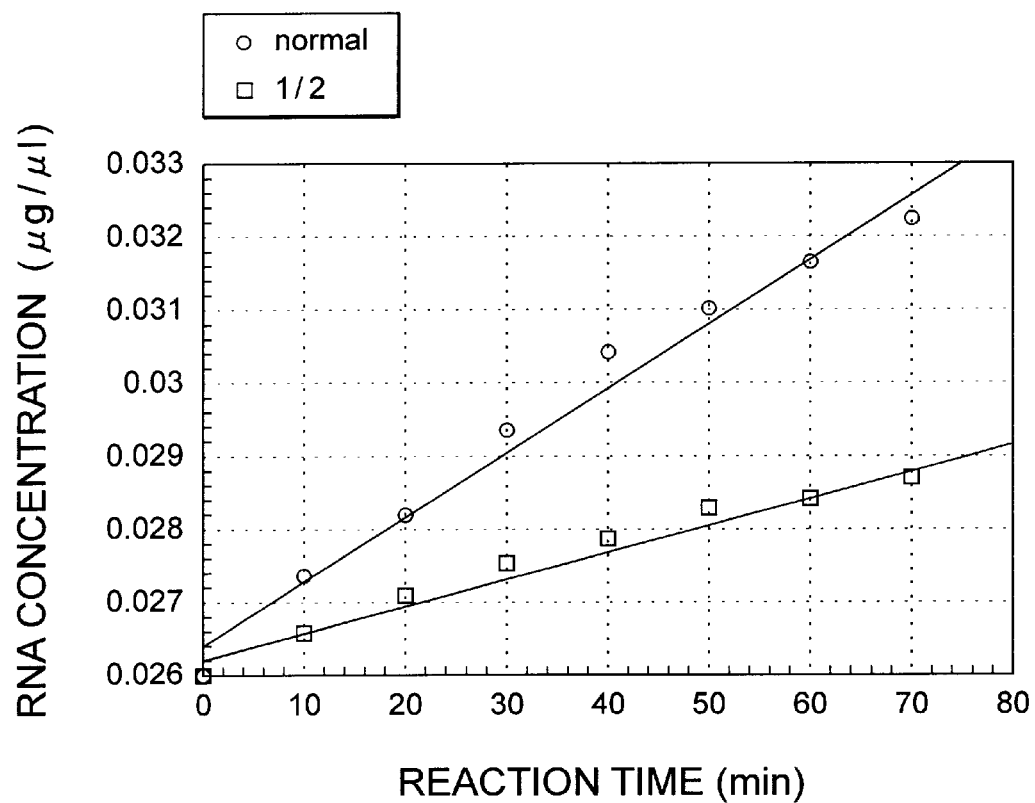
FIG. 16 is a plot showing the confirmation that the quantities of biosynthesized RNA decrease with decreasing amounts of added polymerase.

From FIG. 16, the quantity of the biosynthesized RNA decreases as the quantity of the polymerase decreases. Accordingly, in judging as to whether the rate of transcription reaction is fast or slow, it suffices that the initial period of the reaction be monitored at short intervals and the slope of its time-dependent changes be determined.

Example 7

Effect of Variation of the Amount of Added Probes

XELF-1F donor and acceptor probes having a base sequence complementary to the 5'-terminus of the above-mentioned RNA were added to XELF1-α, which was template DNA, in molar ratios of 200, 400, and 800. Thus the transcription reaction solutions as described below, each 50 µl, were prepared and time-dependent changes in their fluorescence spectra were measured.

(Compositions of the Transcription Reaction Solutions)

| | |
|---|---|
| Template DNA: probes (1:200) | |
| ATP, GTP, CTP, and UTP | each 75 mM |
| XELF1-αDNA | 0.8 pmol |
| 10 × Transcription buffer | 5 µl |
| XELF-1F donor probe | 160 pmol |
| XELF-1F acceptor probe | 160 pmol |
| T3 RNA polymerase | 5 µl |
| Template DNA: probes (1:400) | |
| ATP, GTP, CTP, and UTP | each 75 mM |
| XELF1-αDNA | 0.8 pmol |
| 10 × Transcription buffer | 5 µl |
| XELF-1F donor probe | 320 pmol |
| XELF-1F acceptor probe | 320 pmol |
| T3 RNA polymerase | 5 µl |
| Template DNA: probes (1:800) | |
| ATP, GTP, CTP, and UTP | each 75 mM |
| XELF1-αDNA | 0.8 pmol |
| 10 × Transcription buffer | 5 µl |
| XELF-1F donor probe | 640 pmol |
| XELF-1F acceptor probe | 640 pmol |
| T3 RNA polymerase | 5 µl |

Figure 17:
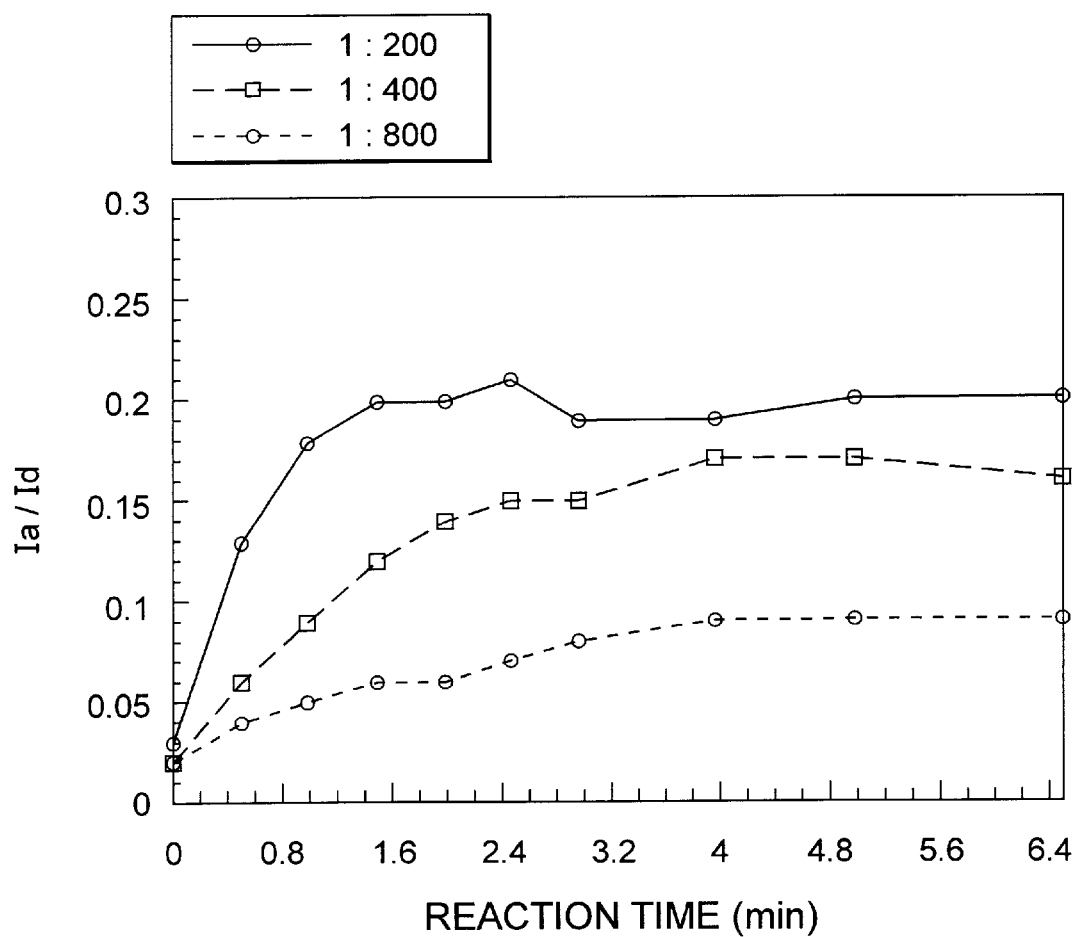
FIG. 17 is a plot showing the time-dependent changes of the transcription reaction for RNA synthesis under conditions where XELF-IF donor and acceptor probes, which hybridize to the vicinity of the 5'-terminus, were added to template DNA in molar ratios of 200, 400, and 800.

On the basis of these results, the ratios of the fluorescence intensities at the fluorescence wavelength of donor to those at the fluorescence wavelength of acceptor were plotted against transcription reaction time (FIG. 17). Where the probes were added to the template DNA in a small excess (1:200), the variation of the Ia/Id value is large at the initial stage of reaction, but there is no variation after about 1.6 hours. In contrast, where the probes were added 400-fold to the template DNA, the fluorescence spectrum continued to change until about 4 hours later. This result indicates that the RNA synthesis takes place not less than 200-fold based on the template. Where the addition was 800-fold, the fluorescence spectrum also continued to change until about 4 hours later. This result indicates that the quantity of the synthesized RNA is between 200-fold and 400-fold based on the template DNA.

Also, where the probes were added to the template DNA in a small excess, the change in the fluorescence spectrum is large at the initial stage of reaction, which allows the transcription reaction to be monitored with great accuracy. On the other hand, where the probes were added to the template DNA in a large excess (1:800), the initial stage of the transcription reaction can not be monitored with great accuracy by means of the fluorescence spectrum because of small variation of the Ia/Id value; but it becomes possible to monitor the end point of the synthetic reaction. Concerning the transcription reaction of the present Examples, it is therefore suggested that the ratio of the template DNA to the probes be set 1:200 for the purpose of monitoring the initial stage of reaction and that the ratio of the template DNA to the probes be set 1:400 or 1:800 for the purpose of monitoring the period toward the termination of transcription reaction.

Example 8

Example Illustrating That the Sites on the RNA to Which the Probes Used in This Invention Hybridize Are Arbitrary The secondary structure of XELF1-αRNA was predicted by computer simulation (DNASIS DNA-Sequence Inputting Analysis System available from Hitachi Soft Engineering Co. Ltd.). The site (base sequence Nos. 184–214) adopting a loop structure that is generally presumed to be hybridized to a probe with ease and the site (base sequence Nos.

346–375) adopting a stem structure that is generally presumed to be hybridized to a probe with difficulty were chosen, respectively. One pair of fluorescence-labeled probes of two types, which have base sequences complementary to the base sequences of those sites, were prepared.

XELF-1F donor probe: having a base sequence complementary to the 184–199 site;

XELF-1F acceptor probe: having a base sequence complementary to the 200–214 site;

XELF-4F donor probe: having a base sequence complementary to the 346–360 site; and XELF-4F acceptor probe: having a base sequence complementary to the 361–375 site.

Figure 18A:
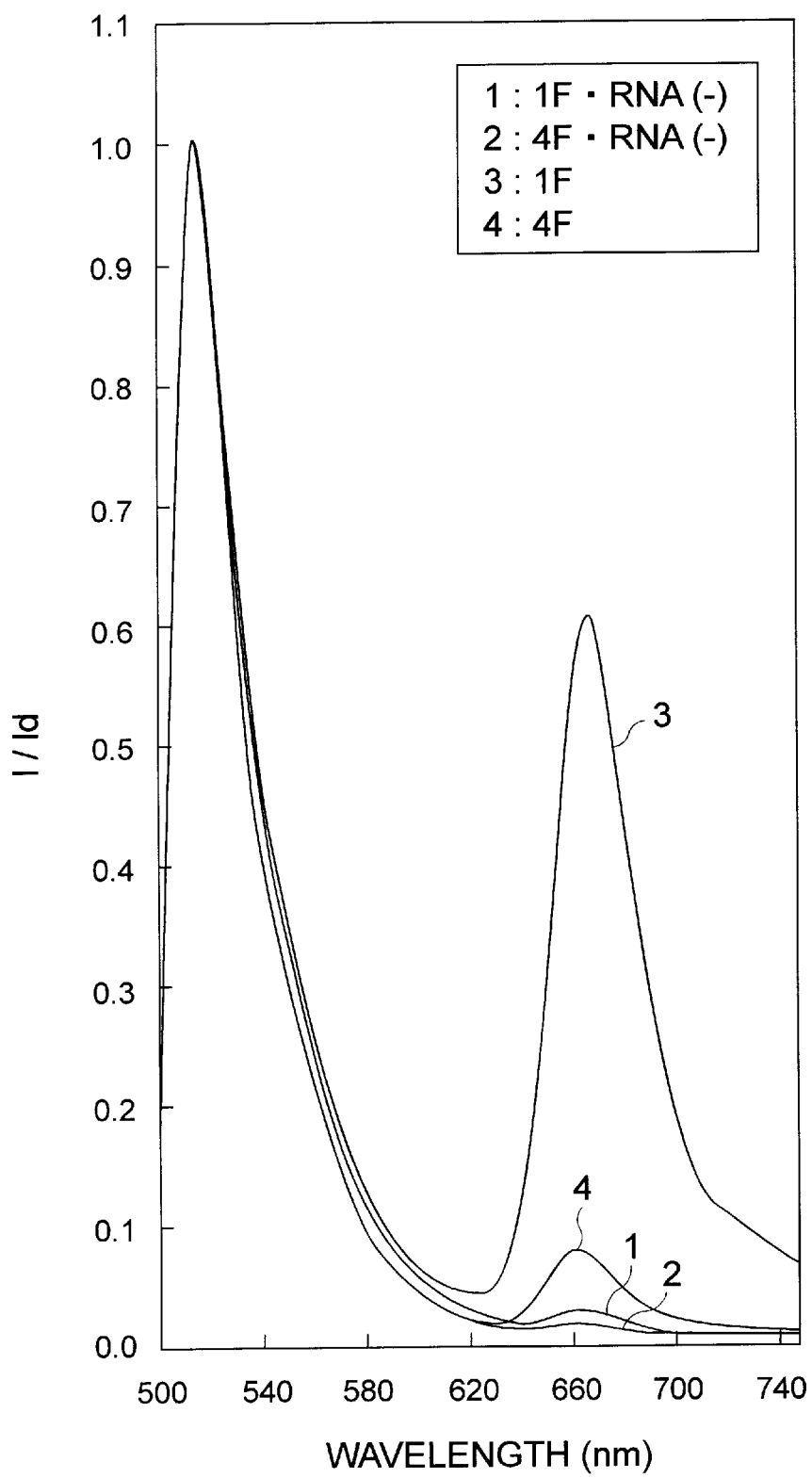
FIG. 18A is a plot showing the results of the fluorescence spectra where XELF1-αRNA was mixed with either XELF-1F probes or XELF-4F probes in a ratio of 1:1 to allow hybridization.

A 1:1 mixed solution of the XELF-1F donor and XELF-1F acceptor probes, and a 1:1 mixed solution of the XELF-4F donor and XELF-4F acceptor probes were prepared, respectively; and their fluorescence spectra were measured. Subsequently, XELF 1-αRNA was respectively added to these solutions in ratios of 1:1 relative to the probes and they were allowed to react at room temperature for 30 min, and then changes in their fluorescence spectra were measured. The results are shown in FIG. 18A. When XELF1-αRNA was added to the XELF-1F probes, a fluorescence spectrum having the greatly enhanced fluorescence quantity of Cy5 was obtained; whereas, the change in the fluorescence spectrum was small when XELF1-αRNA was added to the XELF-4F probes. The changes in fluorescence spectra indicate that resonance energy transfer has occurred between the fluorescence dyes because of hybridization of the probes with the RNA. In other words, the results in FIG. 18A suggest that as the secondary structure of XELF1-αRNA has predicted, the XELF-1F probes well hybridize to XELF1-αRNA while the XELF-4F probes hardly hybridize to XELFI-αRNA.

Thereafter, the method for monitoring an in vitro transcription reaction for RNA synthesis of this invention was conducted using these probes. A transcription reaction solution containing the XELF-1F donor and XELF-1F acceptor probes and a transcription reaction solution containing the XELF-4F donor and XELF-4F acceptor probes were prepared, respectively; and time-dependent changes in their fluorescence spectra were monitored.

(Compositions of the Transcription Reaction Solutions)

| XELF-1F Donor Probe and XELF-1F Acceptor Probe | |
|---|---|
| XELF1-αDNA | 0.8 pmol |
| 10 × Transcription buffer | 5 μl |
| XELF-1F donor probe | 640 pmol |
| XELF-1F acceptor probe | 640 pmol |
| T3 RNA polymerase | 5 μl |
| XELF-4F Donor Probe and XELF-4F Acceptor Probe | |
| XELF1-αDNA | 0.8 pmol |
| 10 × Transcription buffer | 5 μl |
| XELF-4F donor probe | 640 pmol |
| XELF-4F acceptor probe | 640 pmol |
| T3 RNA polymerase | 5 μl |

Figure 18B:
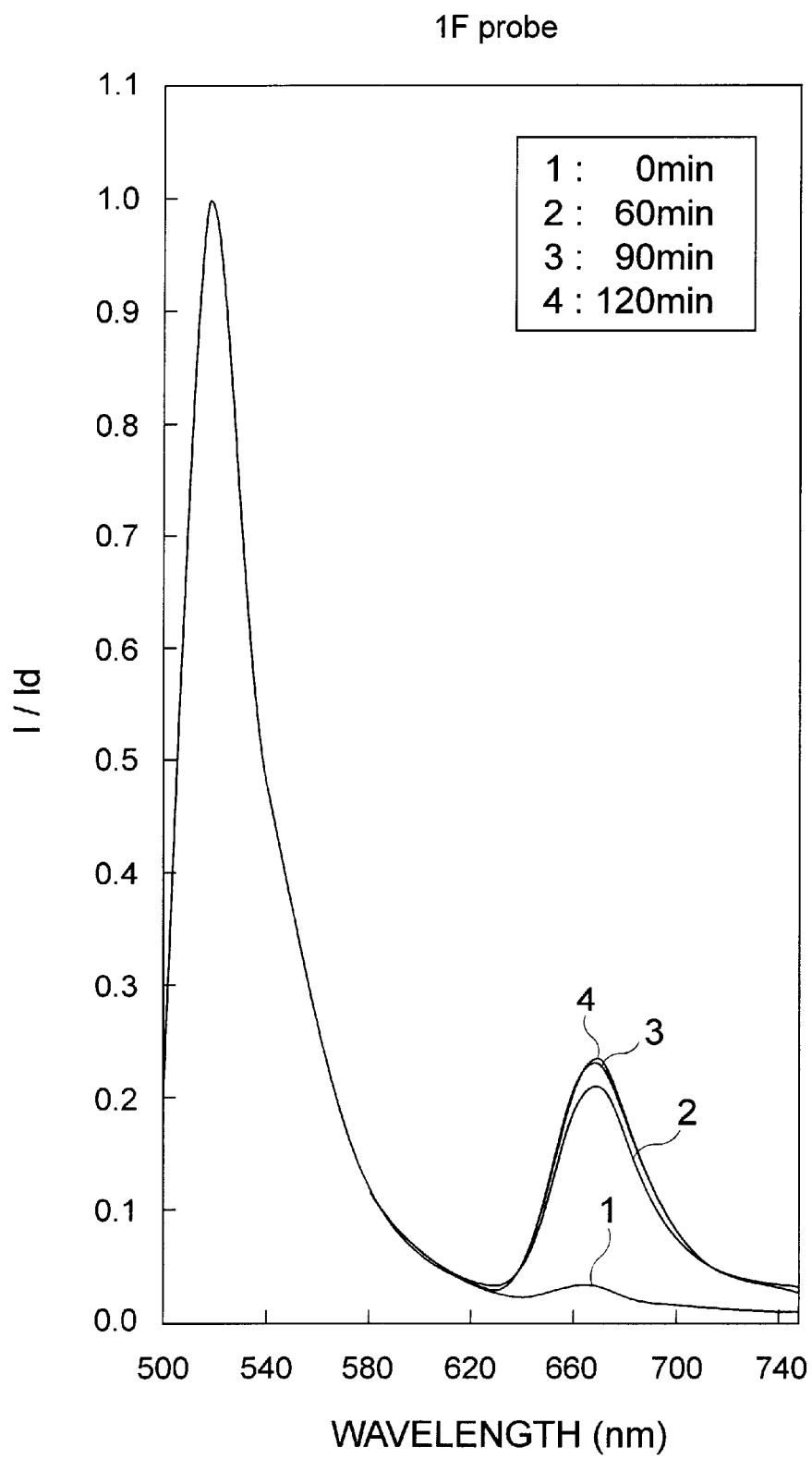
FIG. 18B is a plot showing the results obtained when XELF-1F probes were added to a transcription reaction solution and the time-dependent change of its fluorescence spectrum was measured.
Figure 18C:
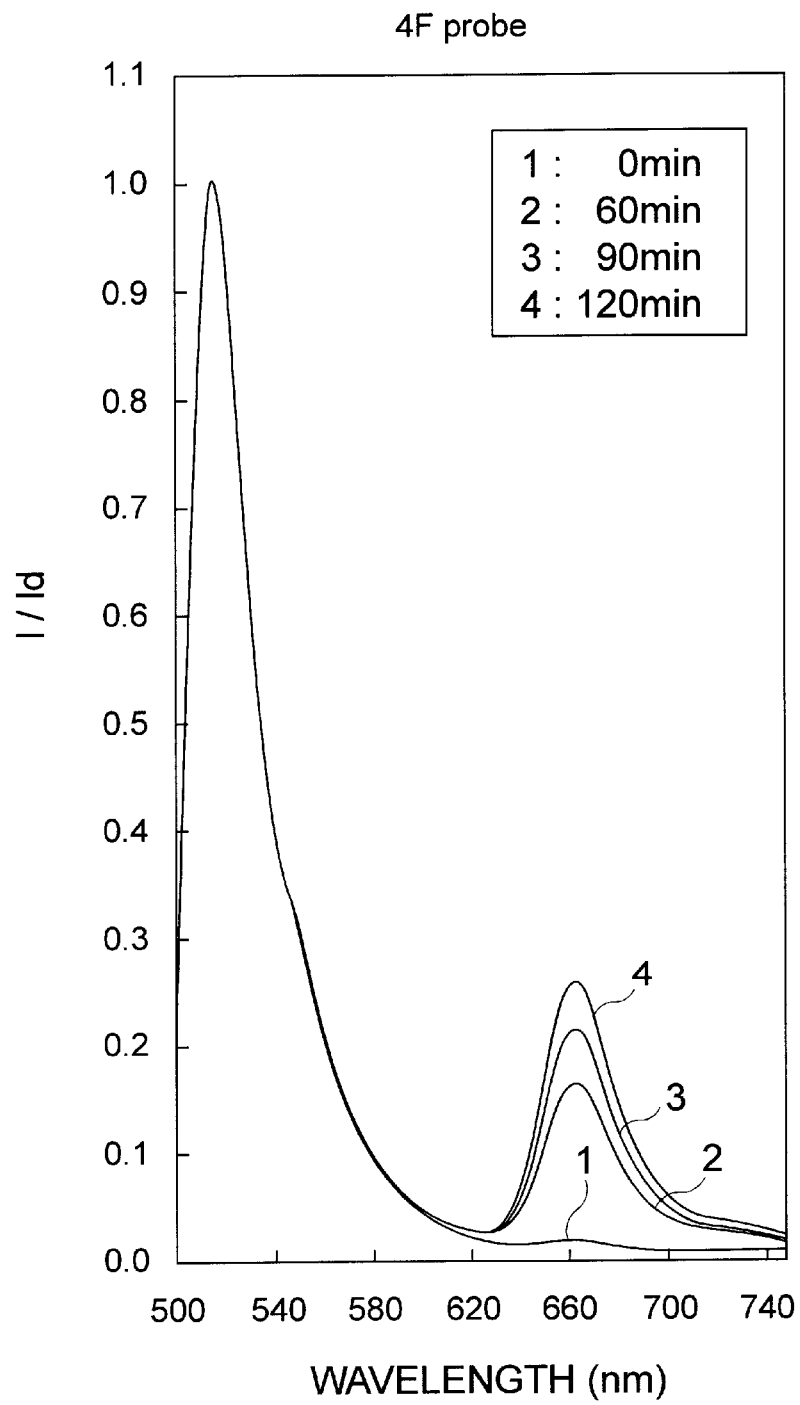
FIG. 18C is a plot showing the results obtained when XELF-4F probes were added to a transcription reaction solution and the time-dependent change of its fluorescence spectrum was measured.

The results are shown in FIGS. 18B and 18C. As is apparent from FIGS. 18B and 18C, when the XELF-4F probes were used, there was also observation of the time-dependent change similar to the case where the XELF-1 F probes were used. These results indicate that even the probes having base sequences, which do not hybridize to RNA with a peculiar secondary structure, will hybridize to the RNA being synthesized if they are added to the transcription reaction solution for the synthesis in advance.

In other words, the probes for use in monitoring a transcription reaction for RNA synthesis according to this invention only have to be provided with a base sequence complementary to part of said RNA; and it will be understood that the selection as to which site on the RNA is subjected to hybridization is arbitrary.

Example 9
Monitoring of In Vitro RNA Transcription for RNA Synthesis by Adjacent Probes For the probes used in the foregoing Examples 1–8, the two types of probes hybridize continuously when they are hybridized to the synthesized RNA.

The probes to be used in this invention are not limited to those which hybridize continuously, and such probes as will hybridize adjacently to each other are also usable: this was ascertained by the following experiments.

(The Probes and Base Sequences Used)
Probes hybridizing continuously:
XELF-1F donor probe (5'-BODIPY493/503-AGCCTTTTCCCATCTC-3' (SEQ ID NO: 1))
XELF-1F acceptor probe (5'-AGGCATACTTG(Cy5)AAGG-3' (SEQ ID NO: 2))
Probes hybridizing adjacently:
XELF-1F donor probe (5'-BODIPY493/503-AGCCTTTTCCCATCTC-3' (SEQ ID NO: 1))
XELF-5F acceptor probe (5'-ACCCAGGCATACTTG(Cy5)-3' (SEQ ID NO: 11))

The single-stranded portion between the probes in their hybrid with the RNA proves to be four bases.

(Compositions of the Transcription Reaction Solutions)
In the case where the continuous probes were used:

| ATP, GTP, CTP, and UTP | each 75 mM |
|---|---|
| XELF1-αDNA | 6 pmol |
| 10 × Transcription buffer | 10 μl |
| XELF-1F donor probe | 432 pmol |
| XELF-5F acceptor probe | 432 pmol |
| T3 RNA polymerase | 10 μl |

Totaled to 100 μl with the DEPEC-treated water.
In the case where the adjacent probes were used:

| ATP, GTP, CTP, and UTP | each 75 mM |
|---|---|
| XELF1-αDNA | 6 pmol |
| 10 × Transcription buffer | 10 μl |
| XELF-1F donor probe | 432 pmol |
| XELF-1F acceptor probe | 432 pmol |
| T3 RNA polymerase | 10 μl |

Totaled to 100 μl with the DEPEC-treated water.

The above reaction solutions were allowed to react at 37° C., and aliquots (each 5 μl) of the reaction solution were collected at predetermined intervals. After their dilution with 145 μl of 1×SSC containing 20 mM EDTA, the measurement of their fluorescence spectra was performed.

Consequently, even when the probes that hybridize adjacently were used, the fluorescence resulting from BODIPY493/503 decreased and that resulting from Cy5 increased as the reaction time lapsed, similarly to the probes that hybridize continuously.

The continuous probes and the adjacent probes were compared with respect to their results obtained by plotting the ratios (Ia/Id) of the fluorescence intensities at 520 nm (Id) to those at 670 nm (Ia): their time-dependent changes in fluorescence intensity were in agreement.

Accordingly, the probes according to this invention are not limited to those that hybridize continuously, and the probes of the two types that hybridize adjacently to part of the RNA can also be employed.

What is claimed is:

1. A method for monitoring initiation and termination of a transcription reaction for RNA synthesis, as well as synthesis of full-length RNA, the method comprising:

carrying out the transcription reaction for RNA synthesis in the presence of a pair of oligonucleotide probes of two types having sequences that hybridize to a part of a sequence of a RNA to be synthesized in the transcription reaction;

measuring fluorescence of the pair of oligonucleotide probes; and evaluating any change in the fluorescence, wherein the pair of oligonucleotide probes comprises a donor probe labeled with an energy donor fluorescent molecule and an acceptor probe labeled with an energy acceptor fluorescent molecule.

2. A method for quantitating RNA synthesized by transcription through a transcription reaction for RNA synthesis, the method comprising:

carrying out the transcription reaction for RNA synthesis in the presence of a pair of oligonucleotide probes of two types having sequences that hybridize to a part of a sequence of a RNA to be synthesized in the transcription reaction;

measuring fluorescence of the pair of oligonucleotide probes; and correlating a change in the fluorescence with a predetermined quantity of the synthesized RNA, wherein the pair of oligonucleotide probes comprises a donor probe labeled with an energy donor fluorescent molecule and an acceptor probe labeled with an energy acceptor fluorescent molecule.

3. A method for simultaneously monitoring initiation of transcription and synthesis of full-length RNA in a transcription reaction for RNA synthesis, the method comprising:

carrying out the transcription reaction for RNA synthesis in the presence of at least two pairs of oligonucleotide probes of two types having sequences that hybridize to a part of a sequence of a RNA to be synthesized in the transcription reaction;

simultaneously measuring fluorescence of the respective pairs of oligonucleotide probes; and evaluating any change in the fluorescence of each of the respective pairs of oligonucleotide probes, wherein the pair of oligonucleotide probes comprises a donor probe labeled with an energy donor fluorescent molecule and an acceptor probe labeled with an energy acceptor fluorescent molecule, and further wherein the respective pairs of oligonucleotide probes hybridize to different sites on the RNA.

4. The method according to claim 3, wherein one pair of the oligonucleotide probes hybridizes in the vicinity of a 5'-terminus of the sequence of the RNA and another pair of the oligonucleotide probes hybridizes in the vicinity of a 3'-terminus of the sequence of the RNA.

* * * * *

```
                         SEQUENCE LISTING

<160> NUMBER OF SEQ ID NOS:  11

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: XELF-IF donor
      probe

<400> SEQUENCE: 1
agccttttcc catctc                                                     16

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: XELF-IF
      acceptor probe

<400> SEQUENCE: 2
aggcatactt gaagg                                                      15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: XELF-2F
      donor probe

<400> SEQUENCE: 3
tcttgatgta tgtgc                                                      15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: XE
      LF-2F acceptor probe

<400> SEQUENCE: 4
ggttgtaacc aatct                                                      15

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: XELF-3F
      donor probe

<400> SEQUENCE: 5
ttaaactctg atggcc                                                     16
```

```
<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: XE
      LF-3F acceptor probe

<400> SEQUENCE: 6
accagtcttt tacta                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: XELF-4F
      donor probe

<400> SEQUENCE: 7
agtaccagtg atcat                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: XE
      LF-4F acceptor probe

<400> SEQUENCE: 8
acagtcagcc tgaga                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: C-FOS
      donor probe

<400> SEQUENCE: 9
tctagttggt ctgtc                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: C-FOS acc
      eptor probe

<400> SEQUENCE: 10
gcagacttct catct                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: XE
      LF-5F acceptor probe

<400> SEQUENCE: 11
acccaggcat acttg                                                    15
```